United States Patent [19]

Imhof et al.

[11] Patent Number: 5,030,636
[45] Date of Patent: Jul. 9, 1991

[54] OCTAHYDROBENZO(F)QUINOLINE DERIVATIVES

[75] Inventors: René Imhof, Gipf-Oberfrick; Hans H. Keller, Basel, both of Switzerland

[73] Assignee: Hoffmann-La Roche Inc., Nutley, N.J.

[21] Appl. No.: 492,693

[22] Filed: Mar. 13, 1990

[30] Foreign Application Priority Data

Mar. 20, 1989 [CH] Switzerland .......................... 1028/89
Dec. 21, 1989 [CH] Switzerland .......................... 4593/89

[51] Int. Cl.$^5$ .................... A61K 31/47; C07D 221/06
[52] U.S. Cl. ...................................... 514/290; 546/101
[58] Field of Search ................... 546/79, 101; 514/290

[56] References Cited

PUBLICATIONS

Chemical Abstracts, vol. 111:23365x, Jul., 1989, Cymerman et al., Synthesis and Dopaminergic Activity of 2-substituted Octahydrobenzo[f]quinolines.

Primary Examiner—Mary C. Lee
Assistant Examiner—Joseph K. McKane
Attorney, Agent, or Firm—George M. Gould; William G. Isgro; Ellen Ciambrone Coletti

[57] ABSTRACT

Compounds of the formula

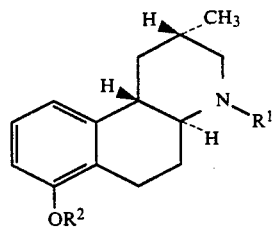

wherein $R^1$ is hydrogen; lower-alkyl, unsubstituted or substituted by hydroxy, lower-alkoxy, cyano, halogen, lower-alkoxycarbonyl, aminocarbonyl, substituted benzoyl or substituted α-hydroxybenzyl; lower-alkenyl; cycloalkyl; cycloalkyl-lower-alkyl; heteroaryl-lower-alkyl; or aryl-lower-alkyl, unsubstituted or substituted by hydroxy, lower-alkoxy, lower-alkyl or halogen, and $R^2$ is hydrogen or lower-alkanoyl, in the form of the racemates and the optical antipodes as well as pharmaceutically acceptable acid addition salts thereof which are active as selective, presynaptically-acting dopamine receptor agonists and are accordingly suitable for the control or prevention of central nervous system illnesses, especially for the control or prevention of psychotic disorders such as chronic schizophrenia, are described. The compounds of formula I can be prepared according to various methods which are known.

35 Claims, No Drawings

OCTAHYDROBENZO(F)QUINOLINE DERIVATIVES

BRIEF SUMMARY OF THE INVENTION

The invention relates to octahydrobenzo[f]quinoline derivatives. In particular, it relates to octahydrobenzo[f]quinolines of the formula

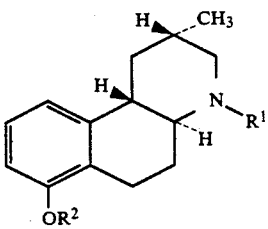

wherein $R^1$ is hydrogen; lower-alkyl, unsubstituted or substituted by hydroxy, lower-alkoxy, cyano, halogen, lower-alkoxycarbonyl, aminocarbonyl, substituted benzoyl or substituted α-hydroxybenzyl; lower-alkenyl; cycloalkyl; cycloalkyl-lower-alkyl; heteroaryl-lower-alkyl; or aryl-lower-alkyl, unsubstituted or substituted by hydroxy lower-alkoxy, lower-alkyl or halogen, and $R^2$ is hydrogen or lower-alkanoyl.

in the form of the racemates and the optical antipodes as well as pharmaceutically acceptable acid addition salts thereof.

The compounds of formula I above as well as their pharmaceutically acceptable acid addition salts are selective, presynaptically-acting dopamine receptor agonists, and are therefore useful in the treatment of psychotic disorders such as chronic schizophrenia.

DETAILED DESCRIPTION OF THE INVENTION

The invention relates to octahydrobenzo[f]quinoline derivatives of the formula

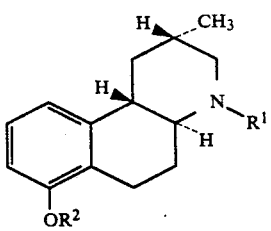

wherein $R^1$ is hydrogen; lower-alkyl, unsubstituted or substituted by hydroxy, lower-alkoxy, cyano, halogen, lower-alkoxycarbonyl, aminocarbonyl, substituted benzoyl or substituted α-hydroxybenzyl; lower-alkenyl; cycloalkyl; cycloalkyl-lower-alkyl; heteroaryl-lower-alkyl; or aryl-lower-alkyl, unsubstituted or substituted by hydroxy, lower-alkoxy, lower-alkyl or halogen, and $R^2$ is hydrogen or lower-alkanoyl, in the form of the racemates and the optical antipodes as well as pharmaceutically acceptable acid addition salts thereof.

It has surprisingly been found that the compounds of formula I possess interesting and therapeutically valuable pharmacodynamic properties with low toxicity. Thus, it has been shown, in animal experiments, that the compounds of formula I above as well as their pharmaceutically acceptable acid addition salts are selective, presynaptically-acting dopamine receptor agonists.

Objects of the invention are the compounds of formula I as well as their pharmaceutically acceptable acid addition salts and as pharmaceutically active substances, medicaments containing a compound of formula I or a pharmaceutically acceptable acid addition salt thereof, the preparation of such medicaments and the use of compounds of formula I as well as their pharmaceutically acceptable acid addition salts in the control or prevention of illnesses or in the improvement of health, especially in the control or prevention of central nervous system illnesses, particularly of psychotic disorders such as chronic schizophrenia. Finally, a process for the preparation of the compounds of formula I above and of their pharmaceutically acceptable acid addition salts as well as intermediates used in this process are objects of the present invention.

The term "lower-alkyl" as used herein—alone or in combination—denotes straight-chain and branched, saturated hydrocarbon residues with 1-8, preferably 1-4, carbon atoms such as methyl, ethyl, n-propyl, isopropyl, n-butyl, isobutyl, sec.-butyl, t-butyl, pentyl, hexyl and the like. The term "lower-alkoxy" denotes lower-alkyl ether groups in which the term "lower-alkyl" has the above significance, such as methoxy, ethoxy, propoxy, isopropoxy, butoxy, isobutoxy, sec.-butoxy, t-butoxy, pentyloxy, hexyloxy and the like. The term "halogen" denotes the four halogens fluorine, chlorine, bromine and iodine. The term "substituted benzoyl" denotes a benzoyl residue which is mono-substituted, preferably in the 4-position, by lower-alkyl, lower-alkoxy or halogen. In a similar manner, the term "substituted α-hydroxybenzyl" denotes an α-hydroxybenzyl residue which is monosubstituted, preferably in the 4-position, by lower-alkyl, lower-alkoxy or halogen. The term "lower-alkenyl" denotes straight-chain and branched, unsaturated hydrocarbon residues with 2-8, preferably 2-4, carbon atoms such as vinyl, allyl and the like. The term "cycloalkyl" denotes saturated, cyclic hydrocarbon residues with 3-8, preferably 3-6, carbon atoms such as cyclopropyl, cyclobutyl, cyclopentyl, cyclohexyl and the like. The term "heteroaryl" denotes a mono- or bicyclic aromatic hydrocarbon residue in which one or more carbon atoms are replaced by 1-2 nitrogen atoms and/or an oxygen or sulfur atom, such as pyrrolyl, furyl, thienyl, imidazolyl, pyrazolyl, oxazolyl, thiazolyl, pyridyl, pyrazinyl, pyrimidinyl, indolyl, quinolyl, isoquinolyl, isoxalinyl and the like. The term "aryl-lower-alkyl" denotes straight-chain or branched lower-alkyl groups in which one or more hydrogen atoms are replaced by phenyl, such as benzyl, diphenylmethyl, trityl, 2-phenylethyl, 3-phenylpropyl, 4-phenylbutyl and the like. The term "lower-alkanoyl" denotes the acid residue of a straight-chain or branched alkanoic acid with 1-8, preferably 1-4, carbon atoms such as formyl, acetyl, propionyl, butyryl, valeryl, isovaleryl and the like.

The term "pharmaceutically acceptable acid addition salts" denotes salts with inorganic and organic acids such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like. Such salts can be prepared readily having regard to the state of the art and taking into consideration the nature of the compound to be converted into a salt.

The compounds of formula I have asymmetric carbon atoms in the 2, 4a and 10b positions, but are present in the relative configuration indicated by formula I, for this reason they are not represented in the form of diastereomers or mixtures of diastereomers, but only in the form of racemates or optical antipodes. The invention embraces the racemates and the optical antipodes. Racemates can be resolved according to usual methods, for example, by column chromatography, thin-layer chromatography, HPLC, fractional crystallization and the like.

Preferred compounds of formula I are those in which $R^2$ is hydrogen or acetyl, preferably hydrogen.

Further preferred compounds of formula I are those in which $R^1$ is hydrogen, lower-alkyl, which is optionally substituted by hydroxy, cyano or substituted benzoyl, cycloalkyl, cycloalkylalkyl or aryl-lower-alkyl, which is optionally substituted by hydroxy.

Compounds of formula I in which $R^1$ is hydrogen, lower-alkyl, which can be optionally substituted by hydroxy, cyano or 4-methoxybenzoyl, with the lower alkyl residue preferably being ethyl, propyl or isopropyl, cyclopentyl, cyclopentylethyl or 4-hydroxyphenethyl are especially preferred.

From the above, it will be evident that of the compounds of formula I especially preferred are those in which $R^1$ is hydrogen, ethyl, propyl or isopropyl, which are optionally substituted by hydroxy, cyano or 4-methoxybenzoyl, cyclopentyl, cyclopentylethyl or 4-hydroxyphenethyl and $R^2$ is hydrogen.

Especially preferred compounds of formula I are:

rac-1, 2, 3, 4, 4aα, 5, 6, 10bβ-octahydro-2α-methyl-4-propylbenzo[f]quinolin-7-ol, rac-1, 2, 3, 4, 4aα, 5, 6, 10bβ-octahydro-4-(4-hydroxyphenethyl)-2α-methylbenzo[f]quinolin-7-ol, rac-1, 2, 3, 4, 4aα, 5, 6, 10bβ-octahydro-7-hydroxy-2α-methylbenzo[f]quinoline-4-ethanol, rac-1, 2, 3, 4, 4aα, 5, 6, 10bβ-octahydro-7-hydroxy-2α-methylbenzo[f]quinoline-4-butyronitrile, rac-1, 2, 3, 4, 4aα, 5, 6, 10bβ-octahydro-4-cyclopentyl-2α-methylbenzo[f]quinolin-7-ol, rac-1, 2, 3, 4, 4aα, 5, 6, 10bβ-octahydro-4-isopropyl-2α-methylbenzo[f]quinolin-7-ol, rac-1, 2, 3, 4, 4aα, 5, 6, 10bβ-octahydro-4-cyclopentyl-ethyl-2α-methylbenzo[f]quinolin-7-ol, rac-[1, 2, 3, 4, 4aα, 5, 6, 10bβ-octahydro-7-hydroxy-2α-methylbenzo[f]quinolin-4-yl]-4'-methoxybutyrohenone, rac-1, 2, 3, 4, 4aα, 5, 6, 10bβ-octahydro-2α-methylbenzo[f]quinolin-7-ol, (-)-1, 2, 3, 4, 4aα, 5, 6, 10bβ-octahydro-4-cyclopentyl-2α-methylbenzo[f]quinolin-7-ol, (-)-1, 2, 3, 4, 4aα, 5, 6, 10bβ-octahydro-2α-methyl-4-propylbenzo[f]quinolin-7-ol, (-)-1, 2, 3, 4, 4aα, 5, 6, 10bβ-octahydro-7-hydroxy-2α-methylbenzo[f]quinoline-4-ethanol and (-)-1, 2, 3, 4, 4aα, 5, 6, 10bβ-octahydro-2α-methylbenzo[f]quinolin-7-ol.

The compounds of formula I and their pharmaceutically acceptable acid addition salts can be prepared in accordance with the invention by a) for the preparation of a compound of formula I in which $R^2$ is hydrogen, cleaving the ether group in a compound of the formula

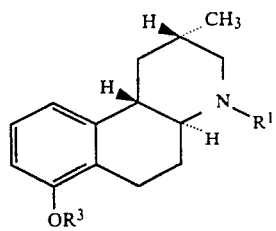

wherein $R^3$ is lower-alkyl and $R^1$ has the significance given above, b) for the preparation of a compound of formula I in which $R^2$ is hydrogen, reductively dehalogenating a compound of the formula

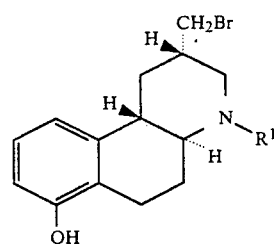

wherein $R^1$ has the significance given above, c) for the preparation of a compound of formula I in which $R^1$ is lower-alkyl, which can be optionally substituted by hydroxy, lower-alooxy, cyano, halogen, lower-alkoxycarbonyl, aminocarbonyl, substituted benzoyl or substituted α-hydroxybenzyl, lower-alkenyl, cycloalkyl, cycloalkyl-lower-alkyl, heteroaryl-lower-alkyl or aryl-lower-alkyl, which is optionally substituted by hydroxy, lower-alkoxy, lower-alkyl or halogen, and $R^2$ is hydrogen, appropriately substituting a compound of formula I in which $R^1$ and $R^2$ each are hydrogen, or d) for the preparation of a compound of formula I in which $R^2$ is lower-alkanoyl, O-acylating a compound of formula I in which $R^2$ is hydrogen, or e) for the preparation of a compound of formula I in which $R^1$ is lower-alkyl, which can be substituted by hydroxy or substituted α-hydroxybenzyl, and $R^2$ is hydrogen, reducing a compound of formula I in which $R^1$ is lower-alkyl, which can be substituted by lower-alkoxycarbonyl or substituted benzoyl, and $R^2$ is hydrogen, or f) for the preparation of a compound of formula I in which $R^1$ and $R^2$ each are hydrogen, debenzylating a compound of formula I in which $R^1$ is benzyl and $R^2$ is hydrogen, and g) if desired, resolving a racemate obtained into the optical antipodes, and/or h) if desired, converting a compound obtained into a pharmaceutically acceptable acid addition salt.

The ether cleavage of a compound of formula II in accordance with process variant a) is effected according to known methods. Thus, the ether cleavage can be carried out, for example, with hydrobromic acid at a temperature between about 50° C. and the reflux temperature, preferably at the reflux temperature, or with phosphorus tribromide in an organic solvent which is inert under the reaction conditions at a temperature between about −10° C. and room temperature, preferably at room temperature. Suitable organic solvents are chlorinated hydrocarbons such as methylene chloride, chloroform or carbon tetrachloride, ethers such as diethyl ether, tetrahydrofuran or dioxane and the like. Methylene chloride is the preferred solvent. It will be appreciated that in this reaction an ether group present in the substituent $R^1$ will also be cleaved.

The reductive dehalogenation of a compound of formula III in accordance with process variant b) is likewise effected in a known manner with hydrogen in the presence of a suitable catalyst, for example, palladium or Raney-nickel. This reaction step is conveniently carried out in the presence of an inert organic solvent or solvent mixture. Suitable solvents are alcohols such as methanol, ethanol or butanol, hydrocarbons such as hexane, benzene, toluene or xylene, ethers such as diethyl ether, tetrahydrofuran or dioxane, alkanoic acids such as acetic acid, and the like. The reaction is preferably carried out at a temperature between about room temperature and the boiling point of the reaction mixture, preferably at room temperature. The pressure is not critical, wherefore for reasons of convenience the reaction is carried out at atmospheric pressure.

The conversion of a compound of formula I in which $R^1$ and $R^2$ each are hydrogen into a corresponding N-substituted compound in accordance with process variant c) is likewise effected according to known methods. Thus, for example, a compound of formula I in which $R^1$ and $R^2$ each are hydrogen can be reacted with an appropriate halide in the presence of an acid-binding agent in an organic solvent which is inert under the reaction conditions. Suitable acid-binding agents are bases such as tertiary amines, for example, triethylamine or ethyldiisopropylamine, sodium carbonate, potassium carbonate and the like. Examples of suitable solvents are ethyl methyl ketone, acetone, methylene chloride, methanol and the like. The reaction is conveniently carried out at a temperature between about room temperature and the reflux temperature of the reaction mixture, preferably at the reflux temperature.

The reaction of a compound of formula I in which $R^2$ is hydrogen with an alkanoylating agent in accordance with process variant d) is likewise effected according to known methods. Suitable alkanoylating agents are lower-alkanoic acid anhydrides and halides, preferably chlorides. The reaction is effected in an organic solvent or solvent mixture which is inert under the reaction conditions at a temperature between about room temperature and the reflux temperature of the reaction mixture, preferably at about room temperature. Suitable solvents are aromatic hydrocarbons such as toluene, chlorinated hydrocarbons such as methylene chloride, acetonitrile and the like. The reaction can be carried out in the presence or absence of an acid-binding agent such as sodium or potassium carbonate, pyridine, triethylamine and the like.

The reduction of a compound of formula I in which $R^{12}$ is lower-alkyl, which is substituted by lower-alkoxycarbonyl or substituted benzoyl, in accordance with process variant e) is likewise carried out according to known methods. Thus, the starting material is conveniently reacted with a complex metal hydride such as lithium aluminum hydride or sodium borohydride and the like in an organic solvent which is inert under the reaction conditions. The reaction conditions depend on the complex metal hydride which is used. Thus, for example, when lithium aluminum hydride is used, the reaction is advantageously carried out in a solvent such as diethyl ether or tetrahydrofuran at the reflux temperature, while the reduction with sodium borohydride is advantageously effected in a solvent such as methanol, ethanol and the like, at about room temperature.

The debenzylation in accordance with process variant f) is likewise effected according to known methods. Conveniently, the debenzylation is effected by hydrogenolysis with hydrogen in the presence of a catalyst such as palladium at about room temperature and atmospheric pressure.

The starting materials of formulas II and III also form part of the invention, and can be prepared according to known methods, such as those compiled in Scheme I hereinafter.

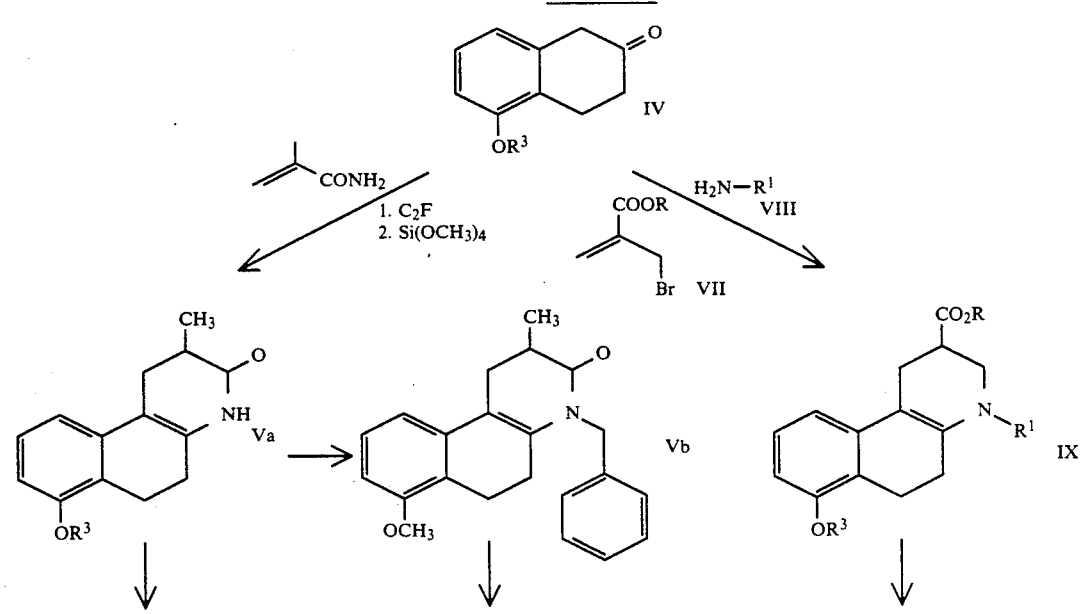

Scheme I

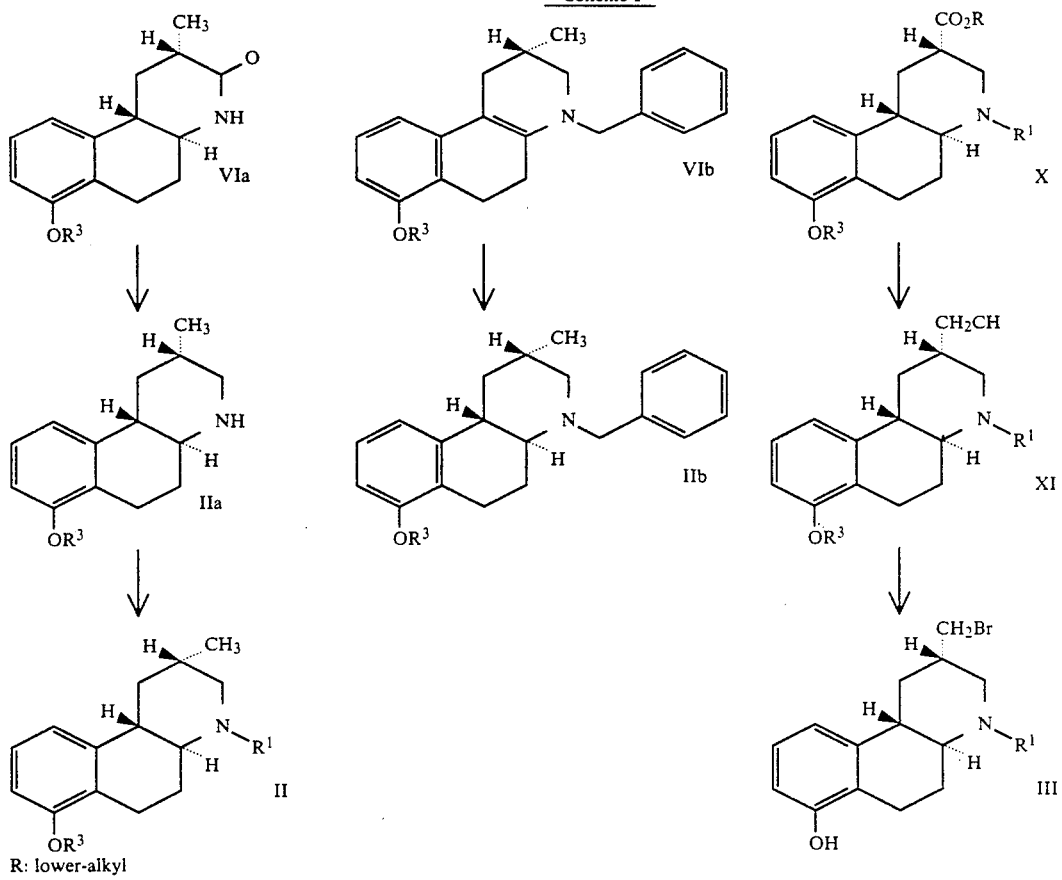

-continued
Scheme I

R: lower-alkyl

For the preparation of the starting materials of formula II, a 2-tetralone of formula IV is reacted firstly with methacrylamide and caesium fluoride and thereafter with tetramethoxysilane. The reactions can be carried out conveniently in an inert organic solvent such as t-butyl methyl ether and the like at a temperature between about room temperature and the reflux temperature of the reaction mixture.

In the next two reaction steps, a compound of formula Va obtained can be reduced to a compound of formula IIa without purification of an intermediately formed compound of formula VIa. The first reduction to a compound of formula VIa can be carried out in an organic solvent which is inert under the reaction conditions, such as methylene chloride and the like, with triethylsilane/trifluoroacetic acid at about room temperature, while the second reduction to a compound of formula IIa is effected in an organic solvent which is inert under the reaction conditions, such as tetrahydrofuran and the like, with lithium aluminum hydride at the reflux temperature.

A compound of formula IIa obtained can then be converted into a corresponding N-substituted compound of formula II under the reaction conditions described for process variant c).

Alternatively, a compound of formula Va obtained can be converted with benzyl chloride under the reaction conditions described for process variant c) into a compound of formula Vb which then, also in two reaction steps, namely a first reduction with lithium aluminum hydride in a solvent such as tetrahydrofuran and the like at the reflux temperature and a second reduction with sodium cyanoborohydride in a solvent mixture such as tetrahydrofuran/acetonitrile or tetrahydrofuran/ethanol at room temperature under acidic reduction conditions, can be reduced to a compound of formula IIb, whereby here the purification of an intermediately formed compound of formula VIb is also not necessary.

For the preparation of a compound of formula III, a 2-tetralone of formula IV can be reacted with an amine of formula VIII and an alkyl 2-(bromomethyl)acrylate of formula VII to give a compound of formula IX. The reaction is preferably effected in an inert organic solvent such as an aromatic hydrocarbon, for example, benzene, at the reflux temperature, whereby the water formed is conveniently collected with a water separator.

A compound of formula IX obtained in this manner can then be reduced to a compound of formula X with preferably sodium cyanoborohydride in an alcohol which corresponds to the alcohol component of the alkyl 2-(bromomethyl)-acrylate.

Reduction of a compound of formula X obtained with lithium aluminum hydride in an inert organic solvent such as an ether, for example, tetrahydrofuran, at preferably room temperature yields a compound of formula XI.

By reacting a compound of formula XI with hydrobromic acid under the reaction conditions given for process variant a), there is obtained a compound of formula III, whereby under these reaction conditions the hydroxymethyl group in the 2-position is simultaneously brominated.

With respect to the precise reaction conditions for the processes for preparing the starting materials described above, reference is made to the experimental section.

The compounds of formulas Va, Vb, VIa, VIb, IX, X and XI are likewise novel and are objects of the present invention. The compounds of formula IV are known or can be obtained in analogy to the preparation of the known compounds.

The compounds of formula I and their pharmaceutically acceptable acid addition salts are active as selective, presynaptically-acting dopamine receptor agonists and are suitable for the control or prevention of central nervous system illnesses, especially for the control or prevention of psychotic disorders such as chronic schizophrenia.

The activity of dopamine receptor agonists can be shown experimentally by means of the tests described hereinafter:

A) Determination of KCl-Induced Dooamine Liberation from Brain Sections

In this in vitro method, described by H. H. Keller and M. Da Prada in European Journal of Pharmacology, 119, 247–250 (1985), isolated brain sections (striatum) of untreated male rats having a body weight of 190–210 g (Füllinsdorfer Albino, SPF) are preincubated with tritium-(-)labelled dopamine. Then, they are superfused in small chambers at 37° C. with physiological buffer and the spontaneously released radioactivity as well as the radioactivity which is inductively released by potassium chloride depolarization both radioactivities being released into the superfusion medium, are measured. The inhibition of the dopamine liberation by the presynaptically-acting dopamine agonists to be tested was determined indirectly in interaction experiments, that is, by the inhibition of the increase in the potassium chloride-induced dopamine liberation brought about by molindone, a presynaptically-acting dopamine antagonist. With respect to this method and its application to dopamine agonists see H. H. Keller et al., Lisuride and other dopamine agonists, Raven Press, New York, 1983, pages 79–87.

B) Determination of the Effect of Dooamine Aoonists on the Homovanillic Acid Content in Rat Brain The test compound is dissolved or suspended, depending on water-solubility, in 0.9% sodium chloride solution (10 ml per kg +2 drops of Tween 80) and administered with the aid of a probang to male rats having a body weight of 140–170 g (Füllindsdorfer Albino, SPF). Two (2) hours later, the animals are decapitated as stress-free as possible without narcosis and their entire brain is deep-frozen at −80° C. Control animals receive only the solvent.

Homovanillic acid is (together with dopamine, 3,4-dihydroxyphenylacetic acid, noradrenalin, 3-methoxy-4-hydroxy-phenylglycol, 5-hydroxytryptamine (serotonin) and 5-hydroxyindoleacetic acid) determined by means of HPLC (high performance liquid chromatography) and electrochemical detection according to the method described by M. Da Prada et al. in Journal of Pharmacology and Experimental Therapeutics 248, 400–414 (1989).

The results obtained in these two tests are compiled in the following Table:

| Compound | Decrease in the Inhibition of the KCl-induced dopamine liberation from sections of rat striatum FSC (nMol) | homovanillic acid (HVA) content in rat brain FSD (mg/kg p.o.) |
| --- | --- | --- |
| A | 30 | 0.3 |
| B | 30 | 0.3 |
| C | <1 | 0.01 |
| D | <10 | 0.1 |
| E | <10 | 0.1 |
| F | 100 | 1.0 |
| G | 100 | 0.3 |

FSC: First significant concentration
FSD: First significant dosage
A: rac-1,2,3,4,4aα,5,6,10bβ-Octahydro-2α-methyl-4-propylbenzo[f]quinolin-7-ol
B: (−)-1,2,3,4,4aα,5,6,10bβ-Octahydro-2α-methyl-4-propylbenzo[f]quinolin-7-ol
C: rac-1,2,3,4,4aα, 5,6,10bβ-Octahydro-4-isopropyl-2α-methylbenzo[f]quinolin-7-ol
D: rac-1,2,3,4,4aα,5,6,10bβ-Octahydro-4-cyclopentyl-2α-methylbenzo[f]quinolin-7-ol
E: (−)-1,2,3,4,4aα,5,6,10bβ-Octahydro-4-cyclopentyl-2α-methylbenzo[f]quinolin-7-ol
F: rac-1,2,3,4,4aα,5,6,10bβ-Octahydro-7-hydroxy-2α-methylbenzo[f]quinoline-4-ethanol
G: (−)-1,2,3,4,4aα,5,6,10bβ-Octahydro-7-hydroxy-2α-methylbenzo[f]quinoline-4-ethanol The compounds of formula I as well as their pharmaceutically acceptable acid addition salts can be used as medicaments, for example, in the form of pharmaceutical preparations. The pharmaceutical preparations can be administered internally, preferably orally, for example, in the form of tablets, coated tablets, dragees, hard and soft gelatin capsules, solutions, emulsions or suspensions, or rectally, for example, in the form of suppositories. The administration can, however, also be effected parenterally such as intramuscularly or intravenously, for example, in the form of injection solutions.

For the preparation of tablets, coated tablets, dragees and hard gelatin capsules, the compounds of formula I as well as their pharmaceutically acceptable acid addition salts can be processed with pharmaceutically inert, inorganic or organic excipients. Lactose, maize starch or derivatives thereof, talc, stearic acid or its salts etc. can be used, for example, as such excipients for tablets, dragees and hard gelatin capsules.

Suitable excipients for soft gelatin capsules are, for example, vegetable oils, waxes, fats, semi-solid and liquid polyols and the like.

Suitable excipients for the preparation of solutions and syrups are, for example, water, polyols, saccharose, invert sugar, glucose and the like.

Suitable excipients for injection solutions are, for example, water, alcohols, polyols, glycerol, vegetable oils and the like.

Suitable excipients for suppositories are, for example, natural or hardened oils, waxes, fats, semi-liquid or liquid polyols and the like.

Moreover, the pharmaceutical preparations can contain preserving agents, solubilizing agents, viscosity-increasing substances, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

In accordance with the invention, the compounds of formula I as well as their pharmaceutically acceptable acid addition salts can be used in the control or prevention of psychotic disorders, especially chronic schizophrenia. The dosage administered can vary within wide limits and will, of course, be fitted to the individual requirements in each particular case. In general, in the case of oral administration a daily dosage of about 10-500 mg, preferably about 20-300 mg, and in the case of parenteral administration a daily dosage of 1-50 mg, preferably 2-25 mg, dispensed in one or more individual doses, should be sufficient. However, the upper limit just mentioned can also be exceeded when this is shown to be indicated. Usually, younger individuals receive half of the adult dosage.

The Examples which follow further illustrate the invention. All temperatures are given in degrees Celsius.

EXAMPLE 1

6.0 g (21.9 mmol) of rac-1, 2, 3, 4, 4aα, 5, 6, 10bβ-octahydro-2α-methyl-4-propyl-7-methoxybenzo[f]quinoline are heated to reflux in 240 ml of hydrobromic acid (48%) while stirring in an argon atmosphere for 1½ hours. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 500 ml of methanol, filtered and acidified with hydrogen chloride in ethanol. Upon concentration of the solution to a volume of 100 ml, there crystallize out 5.56 g (86%) of rac-1, 2, 3, 4, 4aα,5, 6, 10bβ-octahydro-2α-methyl-4-propylbenzo[f]quinolin-7-ol hydrochloride, m.p. 264°-267°.

The rac-1, 2, 3, 4, 4aα, 5, 6, 10bβ-octahydro-2α-methyl-4-propyl-7-methoxybenzo[f]quinoline used as the starting material was prepared as follows:

a) 100 g (0.568 mol) of 5-methoxy-2-tetralone (J. Chem. Soc. 1855 (1949), Cornforth and Robinson) in 500 ml of t-butyl methyl ether are treated with 53 g (0.642 mol) of methacrylamide and 85 g (0.568 mol) of caesium fluoride. Subsequently, 85 ml (0.568 mol) of tetramethoxysilane are added dropwise at 20° within 30 minutes. After heating to reflux for 1 hour, the mixture is cooled and poured into 5 l of water. Extraction with a total of 6 l of methylene chloride yields 125.5 g of reddish crystals which are recrystallized from methylene chloride/ethyl acetate, whereby there are obtained 113.3 g (82%) of rac-1, 2, 5, 6-tetrahydro-2-methyl-7-methoxy[f]quinolin-3(4H)-one as white crystals, m.p. 180°-181°.

b) 113.3 g (0.465 mol) of rac-1, 2, 5, 6-tetrahydro-2-methyl-7-methoxy[f]quinolin-3(4H)-one are dissolved in 1.4 l of methylene chloride and treated at 20° with 222.5 ml (1.4 mol) of triethylsilane. Subsequently, the mixture is cooled to 5° and 555 ml of trifluoroacetic acid are added dropwise thereto at this temperature. The clear solution obtained is stirred at 20° for 63 hours, subsequently poured into 0.5 l of saturated sodium bicarbonate solution and adjusted to PH 9 with 28% sodium hydroxide solution. Extraction with methylene chloride yields 114.9 g of a crystalline residue which is recrystallized from methylene chloride/ethanol/methanol, whereby there are obtained 101.1 g (89%) of rac-1, 2, 4aα,5, 6, 10bβ-hexahydro-2α-methyl-7-methoxybenzo[f]-quinolin-3(4H)-one as white crystals, m.p. 248°-250°.

c) 55.4 g (0.226 mol) of rac-1, 2, 4aα,5, 6, 10bβ-hexahydro-2α-methyl-7-methoxybenzo[f]quinolin-3(4H)-one are added portionwise to a suspension of 17.2 g (0.452 mol) of lithium aluminum chloride in 2 l of tetrahydrofuran and subsequently stirred under reflux for 1 hour. After cooling to 5° the mixture is hydrolyzed with 250 ml of saturated ammonium chloride solution, then 500 ml of ethyl acetate are added thereto and the mixture is filtered over siliceous earth. The filtrate is partitioned between ethyl acetate and water and the organic phase is dried over magnesium sulfate and evaporated under reduced pressure. The residue (53.5 g) is boiled up in 300 ml of diethyl ether, filtered, and the filtrate is diluted with 225 ml of n-hexane. After concentration of this solution to 175 ml, crystallization is effected in a refrigerator at 4°. In this manner, there are obtained 28.5 g (54%) of rac-1, 2, 3, 4, 4aα,5, 6, 10bβ-octahydro-2α-methyl-7-methoxybenzo[f]quinoline as white crystals, m.p. 81°-83°.

d) To a solution of 52 g (22.6 mmol) of rac-1, 2, 3, 4, 4aα, 5, 6, 10bβ-octahydro-2α-methyl-7-methoxybenzo[f]quinoline in 80 ml of methylene chloride are added firstly 4.6 ml of triethylamine and thereafter 2.3 ml (25.9 mol) of propionyl chloride in 15 ml of methylene chloride. The reaction mixture is thereafter stirred at 20° for 5 hours in an argon atmosphere. Subsequently, the mixture is partitioned between saturated sodium bicarbonate solution and methylene chloride, the organic phase is dried with anhydrous magnesium sulfate and the volatile constituents are distilled off under reduced pressure. The residue is chromatographed on silica gel with methylene chloride which contains 2% methanol as the eluting agent. The main component (6.8 g) is dissolved in 60 ml of dry tetrahydrofuran and added dropwise within 30 minutes to a suspension of 1.8 g of lithium aluminum hydride in 100 ml of tetrahydrofuran at 20°-34°. Subsequently, the mixture is heated to reflux for 1 hour, then cooled and hydrolyzed with 20 ml of saturated ammonium chloride solution. After the addition of 50 ml of ethyl acetate, the mixture is stirred at 20° for a further 15 minutes and finally filtered over siliceous earth. The filtrate is partitioned between ethyl acetate and water, the organic phase is dried over anhydrous magnesium sulfate and the volatile constituents are distilled off under reduced pressure. In this manner there are obtained 6.0 g (98%) of rac-1, 2, 3, 4, 4aα, 5, 6, 10bβ-octahydro-2α-methyl-4-propyl-7-methoxybenzo[f]quinoline as a yellow oil which is used directly in the next step.

EXAMPLE 2

3.9 g (13 mmol) of rac-1, 2, 3, 4, 4aα,5, 6, 10bβ-octahydro-2α-methyl-4-(2, 2-dimethylpropyl)-7-methoxybenzo[f]-quinoline are heated to reflux in 150 ml of hydrobromic acid (48%) while stirring in an argon atmosphere for 1 hour. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 150 ml of methanol, filtered and acidified with hydrogen chloride in ethanol. Upon concentration of the solution to a volume of 75 ml, there crystallize out 3.7 g (87%) of rac-1, 2, 3, 4, 4aα,5, 6, 10bβ-octahydro-2α-methyl-4-(2, 2-dimethylpropyl)benzo[f]quinolin-7-ol hydrochloride, m.p. 268°–271°.

The rac-1, 2, 3, 4, 4aα,5, 6, 10bβ-octahydro-2α-methyl-4-(2, 2-dimethylpropyl)-7-methoxybenzo[f]quinoline used as the starting material was obtained in an analogous manner to that described in Example 1d) by reacting rac-1, 2, 3, 4, 4aα, 5, 6, 10bβ-octahydro-2α-methyl-7-methoxybenzo[f]quinoline with pivaloyl chloride and subsequently reducing with lithium aluminum hydride and was used directly in the next step.

EXAMPLE 3

3.6 g (12.5 mmol) of rac-1, 2, 3, 4, 4aα,5, 6, 10bβ-octahydro-2α-methyl-4-butyl-7-methoxybenzo[f]quinoline are heated to reflux in 150 ml of hydrobromic acid (48%) while stirring in an argon atmosphere for 1 hour. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 150 ml of methanol, filtered and acidified with hydrogen chloride in ethanol. Upon concentration of the solution to a volume of 75 ml, there crystallize out 3.5 g (90%) of rac-1, 2, 3, 4, 4aα,5, 6, 10bβ-octahydro-2α-methyl-4-butylbenzo[f]quinolin-7-ol hydrochloride, m.p. 250°–254°.

The rac-1, 2, 3, 4, 4aα,5, 6, 10bβ-octahydro-2α-methyl-4-butyl-7-methoxybenzo[f]quinoline used as the starting material was obtained in an analogous manner to that described in Example 1d) by reacting rac-1, 2, 3, 4, 4aα,5, 6, 10bβ-octahydro-2α-methyl-7-methoxybenzo[f]quinoline with butyryl chloride and subsequently reducing with lithium aluminum hydride and was used directly in the next step.

EXAMPLE 4

3 2 g (13 mmol) of rac-1, 2, 3, 4, 4aα, 5, 6, 10bβ-octahydro-2α-methyl-4-methyl-7-methoxybenzo[f]quinoline are heated to reflux in 150 ml of hydrobromic acid (48%) while stirring in an argon atmosphere for 1½ hours. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 150 ml of methanol, filtered and acidified with hydrogen chloride in ethanol. Upon concentration of the solution to a volume of 50 ml, there crystallize out 2.9 g (83%) of rac-1, 2, 3, 4, 4aα,5, 6, 10bβ-octahydro-2aα-methyl-4-methylbenzo[f]quinoline-7-ol hydrochloride, m.p. 275°–278°.

The rac-1, 2, 3, 4, 4aα,5, 6, 10bβ-octahydro-2α-methyl-4-methyl-7-methoxybenzo[f]quinoline used as the starting material was prepared from rac-1, 2, 3, 4, 4aα,5, 6, 10bβ-octahydro-2aα-methyl-7-methoxybenzo[f]quinoline by reductive methylation with a 1:2 mixture of formaldehyde and formic acid at 100° (2 hours) and was used directly in the next step.

EXAMPLE 5

1.9 g (6.5 mmol) of rac-1, 2, 3, 4, 4aα,5, 6, 10bβ-octahydro-2α-methyl-4-(3-hydroxypropyl)-7-methoxybenzo[f]-quinoline are heated to reflux in 100 ml of hydrobromic acid (48%) while stirring in an argon atmosphere for 2 hours. After cooling, the excess hydrobromic acid is distilled off under reduced pressure. The residue is dissolved in 50 ml of methanol, filtered and treated with 50 ml of ethyl acetate. Upon concentration of the solution to a volume of 25 ml, there crystallize out 1.65 g (61%) of rac-1, 2, 3, 4, 4aα,5, 6, 10bβ-octahydro-2α-methyl-4-(3-bromopropyl)benzo[f]quinolin-7-ol hydrochloride, m.p. 248–251°.

The rac-1, 2, 3, 4, 4aα,5, 6, 10bβ-octahydro-2α-methyl-4-(3-hydroxypropyl)-7-methoxybenzo[f]quinoline used as the starting material was prepared in an analogous manner to that described in Example 30 by reacting rac-1, 2, 3, 4, 4aα,5, 6, 10bβ-octahydro-2α-methyl-7-methoxybenzo[f]quinoline with methyl acrylate and subsequently reducing with lithium aluminum hydride, as described in Example 33, and was used directly in the next step.

EXAMPLE 6

2.7 g (6.8 mmol) of rac-[1, 2, 3, 4, 4aα,5, 6, 10bβ-octahydro-2α-methyl-7-methoxybenzo[f]quinolin-4-yl]-4'-fluoro-butyrophenone are heated to reflux in 400 ml of hydrobromic acid (48%) while stirring in an argon atmosphere for 5 hours. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 10 ml of ethanol, filtered and acidified with hydrogen chloride in ethanol. Upon the addition of 30 ml of ethyl acetate, there crystallize out 2.05 g (62%) of rac-[1, 2, 3, 4, 4aα,5, 6, 10bβ-octahydro-2α-methyl-7-hydroxybenzo[f]quinolin-4-yl]-4'-fluoro-butyrophenone hydrochloride, m.p. 170°–172°.

The rac [1, 2, 3, 4, 4aα,5, 6, 10bβ-octahydro-2α-methyl-7-methoxybenzo[f]quinolin-4-yl]-4'-fluoro-butyrophenone used as the starting material was prepared in an analogous manner to that described in Example 31 by reacting rac-1, 2, 3, 4, 4aα,5, 6, 10bβ-octahydro-2α-methyl-7-methoxybenzo[f]quinoline and 4-chloro-4'-fluorobutyrophenone and was used directly in the next step.

EXAMPLE 7

7.1 g (19.1 mmol) of rac-1, 2, 3, 4, 4aα,5, 6, 10bβ-octahydro-2α-methyl-4-(4-chlorophenethyl)-7-methoxybenzo[f]quinoline are heated to reflux in 400 ml of hydrobromic acid (48%) while stirring in an argon atmosphere for 1 hour. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated.

After two-fold extraction of the aqueous phase with methylene chloride, the organic extracts are combined, dried over anhydrous magnesium sulfate and evaporated under reduced pressure. The residue is dissolved in 200 ml of ethanol, filtered and acidified with hydrogen chloride in ethanol. Upon concentration of the solution to a volume of 50 ml, there crystallize out 5.9 g (79%) of rac-1, 2, 3, 4, 4aα,5, 6, 10bβ-octahydro-2α-methyl-4-(4-chlorophenethyl)benzo[f]-quinolin-7-ol hydrochloride, m.p. 264°–266°.

The rac-1, 2, 3, 4, 4aα,5, 6, 10bβ-octahydro-2α-methyl-4-(4-chlorophenethyl)-7-methoxybenzo[f]quinoline used as the starting material was obtained from rac-1, 2, 3, 4, 4aα, 5, 6, 10bβ-octahydro-2α-methyl-7-methoxybenzo[f]quinoline and 4-chlorophenylacetic acid by acylation (see Synthesis 1983, p. 1013) using borane-trimethylamine in xylene and subsequent reduction of the intermediately formed amide with lithium aluminum hydride and was used directly in the next step.

EXAMPLE 8

3.6 g (10.6 mmol) of rac-1, 2, 3, 4, 4aα,5, 6, 10bβ-octahydro-2α-methyl-4-[2-(2-thienyl)ethyl]-7-methoxybenzo[f]-quinoline are heated to reflux in 400 ml of hydrobromic acid (48%) in an argon atmosphere for 2 hours. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride the organic extracts are combined, dried over anhydrous magnesium sulfate and evaporated under reduced pressure. The residue is dissolved in 200 ml of methanol, filtered and acidified with hydrogen chloride in ethanol. Upon the addition of 50 ml of ethyl acetate and concentration to a volume of 40 ml, there crystallize out 1.95 g (51%) of rac 1, 2, 3, 4, 4aα,5, 6, 10bβ-octahydro-2α-methyl-4-[2-(2-thienyl)ethyl]benzo[f-]quinolin-7-ol hydrochloride, m.p. 276°–279°.

The rac-1, 2, 3, 4, 4aα,5, 6, 10bβ-octahydro-2α-methyl-4-[2-(2-thienyl)ethyl]-7-methoxybenzo[f]quinoline used as the starting material was obtained from rac 1, 2, 3, 4, 4aα, 5, 6, 10bβ-octahydro 2α-methyl-7-methoxybenzo[f]quinoline and thiophene-2-acetic acid by acylation (see Synthesis 1983, p. 1013) using borane-trimethylamine in xylene and subsequent reduction of the intermediately formed amide with lithium aluminum hydride and was used directly in the next step.

EXAMPLE 9

4.2 g (12 mmol) of rac-1, 2, 3, 4, 4aα,5, 6, 10bβ-octahydro-2α-methyl-4-(4-methylphenethyl)-7-methoxybenzo[f]quinoline are heated to reflux in 250 ml of hydrobromic acid (48%) while stirring in an argon atmosphere for 4 hours. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 100 ml of ethanol, filtered and acidified with hydrogen chloride in ethanol. Upon concentration of the solution to a volume of 50 ml, there crystallize out 3.4 g (76%) of rac-1, 2, 3, 4, 4aα,5, 6, 10bβ-octahydro-2α-methyl-4-(4-methylphenethyl)benzo[f]-quinolin-7-ol hydrochloride, m.p. 285°–288°.

The rac-1, 2, 3, 4, 4aα,5, 6, 10bβ-octahydro-2α-methyl-4-(4-methylphenethyl)-7-methoxybenzo[f]quinoline used as the starting material was obtained from rac-1, 2, 3, 4, 4aα,5, 6, 10bβ-octahydro-2α-methyl-7-methoxybenzo[f]quinoline and p-tolylacetic acid by acylation (see Synthesis 1983, p. 1013) using borane-trimethylamine in xylene and subsequent reduction of the intermediately formed amide with lithium aluminum hydride and was used directly in the next step.

EXAMPLE 10

4.25 g (11.6 mmol) of rac-1, 2, 3, 4, 4aα,5, 6, 10bβ-octahydro-2α-methyl-4-(4-methoxyphenethyl)-7-methoxybenzo[f]quinoline are heated to reflux in 250 ml of hydrobromic acid (48%) while stirring in an argon atmosphere for 1½ hours. After cooling the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 100 ml of ethanol, filtered and acidified with hydrogen chloride in ethanol. Upon concentration of the solution to a volume of 50 ml, there crystallize out 3.3 g (76%) of rac-1, 2, 3, 4, 4aα, 5, 6, 10bβ-octahydro-2α-methyl-4-(4-hydroxyphenethyl)benzo[f]-quinolin-7-ol hydrochloride, m.p. 304°–308°.

The rac-1, 2, 3, 4, 4aα,5, 6, 10bβ-octahydro-2α-methyl-4-(4-methoxyphenethyl)-7-methoxybenzo[f]quinoline used as the starting material was obtained from rac-1, 2, 3, 4, 4aα,5, 6, 10bβ-octahydro-2α-methyl-7-methoxybenzo[f]-quinoline and p-methoxyphenylacetic acid by acylation (see Synthesis 1983, p. 1013) using borane-trimethylamine in xylene and subsequent reduction of the intermediately formed amide with lithium aluminum hydride and was used directly in the next step.

EXAMPLE 11

3.55 g (12 mmol) of rac-1, 2, 3, 4, 4aα,5, 6, 10bβ-octahydro-2α-methyl-4-(2-methoxyethyl)-7-methoxybenzo[f]-quinoline are heated to reflux in 140 ml of hydrobromic acid (48%) while stirring in an argon atmosphere for ½ hour. After cooling, the excess hydrobromic acid is distilled off under reduced pressure and the residue is partitioned between methylene chloride and saturated aqueous sodium bicarbonate solution. The aqueous phase is adjusted to pH 9 with 2N sodium hydroxide solution and the organic phase is separated. After two-fold extraction of the aqueous phase with methylene chloride, the organic extracts are combined, dried over anhydrous magnesium sulfate and evaporated under reduced pressure. The residue is dissolved in 50 ml of methanol, filtered and acidified with hydrogen chloride in ethanol. Upon the addition of 2 ml of hydrogen chloride in ethanol (6N), there crystallize out 1.8 g (50%) of rac-1, 2, 3, 4, 4aα,5, 6, 10bβ-octahydro-2α-methyl-7-hydroxybenzo[f]quinoline-4-ethanol hydrochloride, m.p. 252°–253°.

The rac-1, 2, 3, 4, 4aα,5, 6, 10bβ-octahydro-2α-methyl-4-(2-methoxyethyl)-7-methoxybenzo[f]quinoline used as the starting material was obtained in an analogous manner to that described in Example 1d) by reacting rac-1, 2, 3, 4, 4aα,5, 6, 10bβ-octahydro-2α-methyl-7-methoxybenzo[f]quinoline with methoxyacetyl chloride and subsequently reducing with lithium aluminum hydride and was used directly in the next step.

EXAMPLE 12

1.45 g (3.6 mmol) of rac-1, 2, 3, 4, 4aα,5, 6, 10bβ-octahydro-2α-methyl-4-(4-indol-3-ylbutyl)-7-methoxybenzo[f]quinoline in 35 ml of methylene chloride are stirred under an argon atmosphere with 1.1 ml of boron tribromide at −10° for 1 hour and at 10°–15° for 1 hour. Thereafter, 30 ml of 2N sodium hydroxide solution are added dropwise and the mixture is stirred at 20° for a further 15 minutes. The aqueous phase is then adjusted to pH 8 with saturated ammonium chloride solution and the organic phase is separated. After two-fold extraction of the aqueous phase with methylene chloride, the organic extracts are combined, dried over anhydrous magnesium sulfate and evaporated under reduced pressure. The residue is dissolved in 10 ml of ethanol, filtered and acidified with hydrogen chloride in ethanol. Upon the addition of 2 ml of hydrogen chloride in ethanol (6N), there 10bβ-octahydro-2α-methyl-4-(4-indol-3-ylbutyl)benzo[f]-quinolin-7-ol hydrochloride, m.p. 158°–163°.

The rac-1, 2, 3, 4, 4aα,5, 6, 10bβ-octahydro-2α-methyl-4-(4-indol-3-ylbutyl)-7-methoxybenzo[f]quinoline used as the starting material was prepared from rac-1, 2, 3, 4, 4aα,5, 6, 10bβ-octahydro-2α-methyl-7-methoxybenzo[f]quinoline and 4-(3-indolyl)butyric acid by acylation (see Synthesis 1983, p. 1013) using borane-trimethylamine in xylene and subsequent reduction of the intermediately formed amide with lithium aluminum hydride and was used directly in the next step.

EXAMPLE 13

1.05 ml of boron tribromide in 10 ml of methylene chloride are added to a solution of 0.9 g (3.3 mmol) of rac-1, 2, 3, 4, 4aα,5, 6, 10bβ-octahydro-2α-methyl-4-allyl-7-methoxybenzo[f]quinoline in 15 ml of methylene chloride and the mixture is stirred at 20° for 2 hours. Subsequently, 16 ml of 2N sodium hydroxide solution are added dropwise at 0° and the mixture is stirred at 20° for a further ½ hour. The hydrolyzed solution is adjusted to pH 8–9 with ammonium chloride and extracted with methylene chloride. The combined extracts are dried over magnesium sulfate and evaporated. Chromatography of the residue on silica gel with methylene chloride/methanol (98:2) yields 0.65 g of rac-1, 2, 3, 4, 4aα,5, 6, 10bβ-octahydro-2α-methyl-4-allyl-7-hydroxybenzo[f]quinoline which is converted with hydrogen chloride into the hydrochloride, yield 0.66 g (68%), m.p. 267°–270°.

The rac-1, 2, 3, 4, 4aα,5, 6, 10bβ-octahydro-2α-methyl-4-allyl-7-methoxybenzo[f]quinoline used as the starting material was obtained in an analogous manner to that described in Example 1d) by reacting rac-1, 2, 3, 4, 4aα,5, 6, 10bβ-octahydro-2α-methyl-7-methoxybenzo[f]quinoline with acryloyl chloride and subsequently reducing with lithium aluminum hydride and was used directly in the next step.

EXAMPLE 14

3.75 ml of boron tribromide in 30 ml of methylene chloride are added to a solution of 3.9 g (13 mmol) of rac-1, 2, 3, 4, 4aα,5, 6, 10bβ-octahydro-2α-methyl-7-methoxybenzo[f]quinoline-4-butyronitrile in 40 ml of methylene chloride at −10° and the mixture is stirred at 20° for 16 hours. Subsequently, 80 ml of 2N sodium hydroxide solution are added dropwise at 0° and the mixture is stirred at 20° for a further ½ hour. The hydrolyzed solution is adjusted to pH 8–9 with ammonium chloride solution and extracted with methylene chloride. The combined extracts are dried over magnesium sulfate and evaporated. Chromatography of the residue on silica gel with methylene chloride/methanol (99:1) yields 2.65 g of rac-1, 2, 3, 4, 4aα, 5, 6, 10bβ-octahydro-2α-methyl-7-hydroxybenzo[f]quinoline-4-butyronitrile which is converted with hydrogen chloride into the hydrochloride, yield 2.24 g (54%), m.p. 255°–257°.

The rac-1, 2, 3, 4, 4aα, 5, 6, 10bβ-octahydro-2α-methyl-7-methoxybenzo[f]quinoline-4-butyronitrile used as the starting material was prepared in an analogous manner to that described in Example 31 by reacting rac-1, 2, 3, 4, 4aα, 5, 6, 10bβ-octahydro-2α-methyl-7-methoxybenzo[f]quinoline with 4-bromobutyronitrile and was used directly in the next step.

EXAMPLE 15

3 g (13 mmol) of rac-1, 2, 3, 4, 4aα, 5, 6, 10bβ-octahydro-2α-methyl-7-methoxybenzo[f]quinoline in 100 ml of ethyl methyl ketone are heated to reflux for 113 hours with 5.6 ml (52 mmol) of cyclopentyl bromide, 3.6 g of potassium carbonate and 0.9 g of sodium iodide. The volatile constituents are subsequently distilled off under reduced pressure and the residue is partitioned between saturated sodium bicarbonate solution and ethyl acetate. The residue from the organic phase is chromatographed on silica gel (methylene chloride/methanol 98:2, v/v).

The main component from the chromatography (3.15 g) is dissolved in 120 ml of hydrobromic acid (48%) and heated to reflux for 1 hour. After cooling, the volatile constituents are removed under reduced pressure and the residue is partitioned between saturated sodium bicarbonate solution and methylene chloride. After drying the organic phase over magnesium sulfate and evaporation, there are obtained 2.7 g of the crystalline base, m.p. 199°–202°. These are converted with hydrogen chloride in ethanol into the hydrochloride, whereby there are obtained 2.5 g (65%) of rac-1, 2, 3, 4, 4aα, 5, 6, 10bβ-octahydro-2α-methyl-4-cyclopentylbenzo[f]quinolin-7-ol hydrochloride, m.p. >310°.

EXAMPLE 16

3.0 g (13 mmol) of rac-1, 2, 3, 4, 4aα, 5, 6, 10bβ-octahydro-2α-methyl-7-methoxybenzo[f]quinoline in 100 ml of ethyl methyl ketone are heated to reflux for 113 hours with 5.0 ml (52 mmol) of isopropyl bromide, 3.6 g of potassium carbonate and 0.9 g of sodium iodide. Subsequently, the volatile constituents are distilled off under reduced pressure and the residue is partitioned between saturated sodium bicarbonate solution and ethyl acetate. The residue from the organic phase is chromatographed on silica gel (methylene chloride/methanol 97:3).

The main component from the chromatography (2.8 g) is dissolved in 170 ml of hydrobromic acid (48%) and heated to reflux for 1 hour. After cooling, the volatile constituents are removed under reduced pressure and the residue is partitioned between saturated sodium bicarbonate solution and methylene chloride. After drying the organic phase over magnesium sulfate and evaporation, there are obtained 2.6 g of the crystalline base which is converted with hydrogen chloride in ethanol into the hydrochloride, whereby there are obtained 2.94 g (66%) of rac-1, 2, 3, 4, 4aα, 5, 6, 10bβ-octahydro-2α-methyl-4-isopropylbenzo[f]quinolin-7-ol hydrochloride, m.p.>305°.

EXAMPLE 17

3.0 g (13 mmol) of rac-1, 2, 3, 4, 4aα, 5, 6, 10bβ-octahydro-2α-methyl-7-methoxybenzo[f]quinoline in 100 ml of ethyl methyl ketone are heated to reflux for 20 hours with 2.8 ml (26 mmol) of 3-cyclohexylpropyl chloride, 3.6 g of potassium carbonate and 0.9 g of sodium iodide. Subsequently, the volatile constituents are distilled off under reduced pressure and the residue is partitioned between saturated sodium bicarbonate solution and ethyl acetate. The residue from the organic phase is chromatographed on silica gel (methylene chloride/methanol 99:1).

The main component from the chromatography (4.7 g) is dissolved in 180 ml of hydrobromic acid (48%) and heated to reflux for 1 hour. After cooling, the volatile constituents are removed under reduced pressure. The residue is dissolved in 150 ml of hot methanol and 150 ml of hot ethanol, boiled up with active charcoal and filtered over siliceous earth. After concentration under reduced pressure to a volume of 70 ml, there crystallize out 3.2 g (58%) of rac-1, 2, 3, 4, 4aα, 5, 6, 10bβ-octahydro-2α-methyl-4-(3-cyclohexylpropyl)benzo[f]quinolin-7-ol hydrobromide, m.p. 256°-257°.

EXAMPLE 18

2.3 g (10 mmol) of rac-1, 2, 3, 4, 4aα, 5, 6, 10bβ-octahydro-2α-methyl-7-methoxybenzo[f]quinoline in 100 ml of ethyl methyl ketone are heated to reflux for 20 hours with 4.0 g (20 mmol) of 3-phenylpropyl bromide, 3.6 g of potassium carbonate and 0.9 g of sodium iodide. Subsequently, the volatile constituents are distilled off under reduced pressure and the residue is partitioned between saturated sodium bicarbonate solution and ethyl acetate. The residue from the organic phase is chromatographed on silica gel (methylene chloride/methanol 99:1).

The main component from the chrOmatography (4.35 g) is dissolved in 200 ml of hydrobromic acid (48%) and heated to reflux for 1 hour. After cooling, the volatile constituents are removed under reduced pressure and the residue is partitioned between saturated sodium bicarbonate solution and methylene chloride. After drying the organic phase over magnesium sulfate and evaporation, there are obtained 3.15 g of the crystalline base which are converted with hydrogen chloride in ethanol into the hydrochloride, whereby there are obtained 3.19 g (86%) of rac-1, 2, 3, 4, 4aα, 5, 6, 10bβ-octahydro-2α-methyl-4-(3-phenylpropyl)benzo[f]quinolin-7-ol hydrochloride, m.p. 264°-270°.

EXAMPLE 19

3.0 g (13 mmol) of rac-1, 2, 3, 4, 4aα, 5, 6, 10bβ-octahydro-2α-methyl-7-methoxybenzo[f]quinoline in 100 ml of ethyl methyl ketone are heated to reflux for 20 hours with 5 g (26 mmol) of 2-cyclohexylethyl bromide, 3.6 g of potassium carbonate and 0.9 g of sodium iodide. Subsequently, the volatile constituents are distilled off under reduced pressure and the residue is partitioned between saturated sodium bicarbonate solution and ethyl acetate The residue from the organic phase is chromatographed on silica gel (methylene chloride/methanol 98:2).

The main component from the chromatography (3.65 g) is dissolved in 200 ml of hydrobromic acid (48%) and heated to reflux for 1 hour. After cooling, the volatile constituents are removed under reduced pressure and the residue is partitioned between saturated sodium bicarbonate solution and methylene chloride. After drying the organic phase over magnesium sulfate and evaporation, there are obtained 3.4 g of the base which are converted with hydrogen chloride in ethanol into the hydrochloride, whereby there are obtained 2.9 g (57%) of rac-1, 2, 3, 4, 4aα, 5, 6, 10bβ-octahydro-2α-methyl-4-(2-cyclohexylethyl)-benzo[f]quinolin-7-ol hydrochloride, m.p. 278°-280°.

EXAMPLE 20

3.0 g (13 mmol) of rac-1, 2, 3, 4, 4aα, 5, 6, 10bβ-octahydro-2α-methyl-methoxybenzo[f]quinoline in 100 ml of ethyl methyl ketone are heated to reflux for 20 hours with 6.53 g (26 mmol) of 4-chloro-1-(4-t-butylphenyl)-1-butanone (95%), 3.6 g of potassium carbonate and 0.9 g of sodium iodide. Subsequently, the volatile constituents are distilled off under reduced pressure and the residue is partitioned between saturated sodium bicarbonate solution and ethyl acetate. The residue from the organic phase is chromatographed on silica gel (ethl acetate/n-hexane 1:1).

The main component from the chromatography (4.2 g) is dissolved in 300 ml of hydrobromic acid (48%) and heated to reflux for 3½ hours. After cooling, the volatile constituents are removed under reduced pressure and the residue is partitioned between saturated sodium bicarbonate solution and methylene chloride. After drying the organic phase over magnesium sulfate and evaporation, there are obtained 3.95 g of the base which are converted in 100 ml of ethyl acetate with hydrogen chloride in ethanol into the hydrochloride, whereby there are obtained 2.75 g (46%) of rac-1, 2, 3, 4, 4aα, 5, 6, 10bβ-octahydro-2α-methyl-4-(4'-t-butyl-4-phenyl-4-oxobutyl)benzo[f]quinolin-7-ol hydrochloride, m.p. 170°-172°.

EXAMPLE 21

3.0 g (13 mmol) of rac-1, 2, 3, 4, 4aα, 5, 6, 10bβ-octahydro-2α-methyl-7-methoxybenzo[f]quinoline in 100 ml of dimethylformamide are heated to reflux for 120 hours with 6.3 ml (52 mmol) of cyclohexyl bromide, 3.6 g of potassium carbonate and 0.9 g of sodium iodide. Subsequently, the volatile constituents are distilled off under reduced pressure and the residue is partitioned between saturated sodium bicarbonate solution and ethyl acetate. The residue from the organic phase is chromatographed on silica gel (firstly ethyl acetate/n-hexane 1:3, then ethyl acetate).

The main component from the chromatography (1.5 g) is dissolved in 100 ml of hydrobromic acid (48%) and heated to reflux for 2 hours. After cooling, the volatile constituents are removed under reduced pressure and the residue is partitioned between saturated sodium bicarbonate solution and methylene chloride. After drying the organic phase over magnesium sulfate and evaporation, there are obtained 1.3 g of the base which are converted with hydrogen chloride in ethanol into the hydrochloride, whereby there is obtained 0.95 g (22%) of rac-1, 2, 3, 4, 4aα, 5, 6, 10bβ-octahydro-2α- methyl-4-cyclohexylbenzo[f]-quinolin-7-ol hydrochloride, m.p.>305°.

EXAMPLE 22

3.0 g (13 mmol) of rac-1, 2, 3, 4, 4aα, 5, 6, 10bβ-octahydro-2α-methyl-7-methoxybenzo[f]quinoline in 100 ml of ethyl methyl ketone are heated to 150° in an autoclave for 5 days with 5.0 g (37 mmol) of cyclobutyl bromide, 3.6 g of potassium carbonate and 0.9 g of sodium iodide. Subsequently, the volatile constituents are distilled off under reduced pressure and the residue is partitioned between saturated sodium bicarbonate solution and ethyl acetate. The crude product is dissolved in 300 ml of hydrobromic acid (48%) and heated to reflux for 5 hours. After cooling, the volatile constituents are removed under reduced pressure and the residue is partitioned between saturated sodium bicarbonate solution and methylene chloride. After drying the organic phase over magnesium sulfate and evaporation, there are obtained 3.35 g of the base which are chromatographed on silica gel (methylene chloride/methanol 96:4 to 92:8). The main component (1.5 g) is converted with hydrogen chloride in ethanol into the hydrochloride, whereby there are obtained 1.05 g 23%) of rac-1, 2, 3, 4, 4aα, 5, 6 10bβ-octahydro-2α-methyl(4-cyclobutylbenzo[f]quinolin-7-ol hydrochloride, m.p. 280°-283°.

EXAMPLE 23

3.0 g (13 mmol) of rac-1, 2, 3, 4, 4aα, 5, 6, 10bβ-octahydro-2α-methyl-7-methoxybenzo[f]quinoline in 100 ml of ethyl methyl ketone are heated to 150° in an autoclave for 72 hours with 5.1 g (26 mmol) of 4-chloro-1-(4-methylphenyl)-1-butanone, 3.6 g of potassium carbonate and 0.9 g of sodium iodide. Subsequently, the volatile constituents are distilled off under reduced pressure and the residue is partitioned between saturated sodium bicarbonate solution and ethyl acetate. The residue from the organic phase is chromatographed on silica gel (firstly ethyl acetate/n-hexane 1:3, then ethyl acetate).

The main component from the chromatography (1.3 g) is dissolved in 150 ml of hydrobromic acid (48%) and heated to reflux for 5 hours. After cooling, the volatile constituents are removed under reduced pressure and the residue is partitioned between saturated sodium bicarbonate solution and methylene chloride. After drying the organic phase over magnesium sulfate and evaporation, there are obtained 1.2 g of the base which are converted with hydrogen chloride in ethanol into the hydrochloride, whereby there is obtained 0.73 g (15%) of rac-1, 2, 3, 4, 4aα, 5, 6, 10bβ-octahydro-2α-methyl-4-(4-methylphenyl)-4-oxobutyl)benzo[f]quinolin-7-ol hydrochloride, m.p. 173°-175°.

EXAMPLE 24

2.94 g (15.6 mmol) of (-)-1, 2, 3, 4, 4aα, 5, 6, 10bβ-octahydro-2α-methyl-7-methoxybenzo[f]quinoline in 120 ml of ethyl methyl ketone are heated to reflux for 72 hours with 10.05 ml (93.3 mmol) of cyclopentyl bromide, 8.6 g of potassium carbonate and 1 g of sodium iodide. Subsequently, the cooled reaction solution is poured into 100 ml of water and extracted twice with 100 ml of ethyl acetate. The organic phase, dried over magnesium sulfate, is evaporated under reduced pressure and the residue is chromatographed on silica gel with methylene chloride/methanol (98:2) as the eluting agent.

The main component from the chromatography (3.0 g) is heated to reflux for 2 hours in 110 ml of hydrobromic acid. After cooling, the volatile constituents are distilled off under reduced pressure. The residue is suspended in 70 ml of methanol and 300 ml of methylene chloride and 2N sodium hydroxide solution is added to the suspension while stirring until a solution is obtained. Subsequently, the pH value of the solution is adjusted to 8 with saturated ammonium chloride solution and extracted with methylene chloride. The organic phase, dried over magnesium sulfate, is evaporated. The residue is dissolved in 100 ml of methanol and 100 ml of ethanol and acidified with alcoholic hydrogen chloride solution and concentrated to a volume of about 30 ml, whereby 2.4 g (49%) of beige crystals of (-)-1, 2, 3, 4, 4aα, 5, 6, 10bβ-octahydro -2α-methyl-4-cyclopentylbenzo[f]quinolin-7-ol hydrochloride crystallize out, m.p. 284°-289°; $[α]_D = -38.0°$ (c=1% in methanol).

The (-)-1, 2, 3, 4, 4aα, 5, 6, 10bβ-octahydro-2α-methyl-7-methoxybenzo[f]quinoline used as the starting material was prepared as follows:

To a solution of 24.8 g (106 mmol) of rac-1, 2, 3, 4, 4aα, 5, 6, 10bβ-octahydro-2α-methyl-7-methoxybenzo[f]quinoline in 500 ml of methylene chloride and 50 ml of water are simultaneously added dropwise from two dropping funnels while stirring 21.9 g (118 mmol) of R-(-)-α-methoxyphenylacetyl chloride [prepared from R-(-)-α-methoxyphenylacetic acid and oxalyl chloride by heating to reflux for 1 hour in methylene chloride] in 50 ml of methylene chloride and 500 ml of 5% sodium hydroxide solution and the mixture is subsequently stirred at 20° for a further 15 hours. For the working-up, the reaction mixture is partitioned between 500 ml of methylene chloride and 500 ml of saturated sodium chloride solution. The organic phase is dried over anhydrous magnesium sulfate and evaporated under reduced pressure. The residual resin (34 g) is chromatographed on 1.2 kg of silica gel. There are obtained as fraction 1 12.6 g (eluted with diethyl ether/n-hexane 1:3) and as fraction 2 10.1 g (eluted with diethyl ether/n-hexane 1:1) of the diastereomeric amides of R-(-)-α-methoxyphenylacetic acid.

10.1 g (26.6 mmol) of fraction 2 are dissolved in 1.9 l of tetrahydrofuran and then treated with 41.6 g of potassium t-butylate and 3.4 ml of water and heated to reflux for 1 hour. After cooling, the mixture is partitioned between diethyl ether and 2N sodium hydroxide solution and the organic phase is washed with saturated sodium chloride solution and dried over anhydrous magnesium sulfate. After concentration under reduced pressure, there are obtained 6.1 g of (-)-1, 2, 3, 4, 4aα, 5, 6, 10bβ-octahydro-2α-methyl-7-methoxybenzo[f]quinoline which crystallizes as the hydrochloride from methanol/ethyl acetate, m.p. 190°-193°, $[α]D = -85.5°$ (c=1% in methanol).

From fraction 1, there is obtained in an analogous manner (+)-1, 2, 3, 4, 4aα, 5, 6, 10bβ-octahydro-2α-methyl-7-methoxybenzo[f]quinoline which crystallizes as the hydrochloride from methanol/ethyl acetate, m.p. 193°-194°, $[α]D = +87.4°$ (c=1% in methanol).

EXAMPLE 25

5.0 g (20.5 mmol) of rac-1, 2, 5, 6-tetrahydro-2-methyl-7-methoxybenzo[f]quinolin-3(4H)-one are heated to reflux for 1/4 hour with 3 g (27.1 mmol) of potassium t-butylate in 80 ml of t-butyl alcohol and, after the addition of 2.4 ml (20.5 mmol) of benzyl chloride, held at this temperature for a further 3 hours. After cooling, the mixture is partitioned between water and diethyl ether and the organic phase is dried over magnesium sulfate. Upon evaporation, there crystallize out 5.5 g (81%) of rac-1, 2, 5, 6-tetrahydro-2-methyl-4-benzyl-7-methoxybenzo[f]quinolin-3-one, m.p. 136°–137°.

5.5 g (16.5 mmol) of rac-1, 2, 5, 6-tetrahydro-2-methyl-4-benzyl-7-methoxybenzo[f]quinolin-3-one in 200 ml of tetrahydrofuran are reduced at reflux temperature for 2 hours with 1.3 g of lithium aluminum hydride in 100 ml of dry tetrahydrofuran. After cooling, 100 ml of ammonium chloride solution are added dropwise at 10°. The hydrolyzed solution is filtered over siliceous earth and the filtrate is partitioned between diethyl ether and water. After drying the organic phase over magnesium sulfate, it is evaporated under reduced pressure, whereby there are obtained 6.45 g of yellow oil (20.2 mmol). This is dissolved in 50 ml of acetonitrile and treated portionwise at 20° with 2.05 g (32.8 mmol) of sodium cyanoborohydride, whereby the pH value is held at the transition point of bromocresol green with 6.3N hydrogen chloride in ethanol (total 6.2 ml). After a reaction period of 16 hours, excess reagent is destroyed with a small amount of concentrated hydrochloric acid and the mixture is subsequently poured on to ice. The mixture is adjusted to pH 9 with 2N sodium hydroxide solution and extracted with diethyl ether. Drying of the organic phase over magnesium sulfate and distillation of the volatile constituents under reduced pressure leads to a crude product (6.3 g) which is chromatographed on silica gel. With diethyl ether/n-hexane (1:4), there are eluted 2.6 g of rac-1, 2, 3, 4, 4a$\alpha$, 5, 6, 10b$\beta$-octahydro-2$\alpha$-methyl-4-benzyl-7methoxybenzo[f]quinoline as a pale yellow oil. (Hydrochloride from ethyl acetate/ethanol, m.p. 214°–215°).

2.6 g (8.1 mmol) of rac-1, 2, 3, 4, 4a$\alpha$, 5, 6, 10b$\beta$-octahydro-2$\alpha$-methyl-4-benzyl-7-methoxybenzo[f]quinoline is heated to reflux for 3½ hours with 100 ml of hydrobromic acid (48%). After cooling, the volatile constituents are evaporated under reduced pressure and the residue is partitioned between saturated sodium bicarbonate solution and methylene chloride. Drying of the organic phase over magnesium sulfate and concentration yields 2.4 g (47%) of crystalline rac-1, 2, 3, 4, 4a$\alpha$, 5, 6, 10b$\beta$-octahydro-2$\alpha$-methyl-4-benzylbenzo[f]quinolin-7-ol, m.p. 174°–178°. Crystallization from hydrogen bromide/ethanol yields the hydrobromide, m.p. 293°–294°.

EXAMPLE 26

2.4 g (7.8 mmol) of rac-1, 2, 3, 4, 4a$\alpha$, 5, 6, 10b$\beta$-octahydro-2$\alpha$-methyl-4-benzylbenzo[f]quinolin-7-ol are dissolved in 200 ml of methanol and hydrogenated at 20° for 2 hours and at atmospheric pressure in the presence of 0.25 g of palladium/carbon (10%). Subsequently, the catalyst is filtered off. The filtrate is evaporated and the product is crystallized from hydrogen chloride/ethanol. In this manner, there are obtained 1.55 g (78%) of rac-1, 2, 3, 4, 4a$\alpha$, 5, 6, 10b$\beta$-octahydro-2$\alpha$-methylbenzo[f]quinolin-7-ol hydrochloride, m.p.>285°.

EXAMPLE 27

2.0 g (9.2 mmol) of rac-1, 2, 3, 4, 4a$\alpha$, 5, 6, 10b$\beta$-octahydro-2$\alpha$-methylbenzo[f]quinolin-7-ol are dissolved in 100 ml of methanol, treated with 0.91 ml (13.8 mmol) of acrylonitrile and heated to reflux for 17 hours. Subsequently, the volatile constituents are evaporated under reduced pressure and the residue is chromatographed on silica gel with a 98:2 mixture of methylene chloride and methanol as the eluting agent. As the main component, there are obtained 2.0 g of rac-1, 2, 3, 4, 4a$\alpha$, 5, 6, 10b$\beta$-octahydro-7-hydroxy-2$\alpha$-methylbenzo[f]quinoline-4-propionitrile which are converted with 5N hydrogen chloride in ethanol into the hydrochloride, m.p.>312°, yield 2.1 g (74%).

EXAMPLE 28

4.9 g (22.5 mmol) of rac-1, 2, 3, 4, 4a$\alpha$, 5, 6, 10b$\beta$-octahydro-2$\alpha$-methylbenzo[f]quinolin-7-ol are dissolved in 200 ml of methanol, treated with 24 g (33.8 mmol) of acrylamide and heated to reflux for 30 hours. Subsequently, the volatile constituents are evaporated under reduced pressure and the residue is chromatographed on silica gel with a 92:8 mixture of methylene chloride and methanol as the eluting agent. As the main component, there are obtained 5.9 g of rac-1, 2, 3, 4, 4a$\alpha$, 5, 6, 10b$\beta$-octahydro-7-hydroxy-2$\alpha$-methylbenzo[f]quinoline-4-propionamide which are converted with 5N hydrogen chloride in ethanol into the hydrochloride, m.p. 250°, yield 4.5 g (62%).

EXAMPLE 29

4.0 g (18.4 mmol) of rac-1, 2, 3, 4, 4a$\alpha$, 5, 6, 10b$\beta$-octahydro-2$\alpha$-methylbenzo[f]quinolin-7-ol are dissolved in 200 ml of methylene chloride and treated with 5.1 ml of triethylamine. To the solution, there are added dropwise at 20° 2.4 g (22.1 mmol) of methoxyacetyl chloride in 15 ml of methylene chloride. After stirring at 20° for 20 hours, the mixture is partitioned between saturated sodium bicarbonate solution and methylene chloride, backextracted with methylene chloride. The organic phase is dried over magnesium sulfate and evaporated under reduced pressure. The resinous residue (5.6 g) is dissolved in 60 ml of dry tetrahydrofuran and added dropwise to a suspension of 1.25 g of lithium aluminum hydride in 50 ml of dry tetrahydrofuran. After heating to reflux for 1 hour, the mixture is cooled to 10° and 20 ml of saturated ammonium chloride solution are added dropwise thereto. Subsequently, 50 ml of ethyl acetate are added while stirring and the mixture is finally filtered over siliceous earth. After drying over magnesium sulfate and distillation of the solvent, the residue is dissolved in 30 ml of ethanol and treated with 10 ml of 6N hydrogen chloride in ethanol, whereby there are obtained 4.35 g (76%) of rac-1, 2, 3, 4, 4a$\alpha$, 5, 6, 10b$\beta$-octahydro-4-(2-methoxyethyl)-2$\alpha$-methylbenzo[f]quinolin-7-ol hydrochloride, m.p. 243°–245°.

EXAMPLE 30

3.5 g (13 mmol) of rac-1, 2, 3, 4, 4a$\alpha$, 5, 6, 10b$\beta$-octahydro-2$\alpha$-methylbenzo[f]quinolin-7-ol are dissolved in 150 ml of methanol, treated with 1.14 g (19 mmol) of methyl acrylate and heated to reflux for 20 hours. Subsequently, the volatile constituents are evaporated under reduced pressure and the residue is chromatographed on silica gel with a 98:2 mixture of methylene chloride and methanol as the eluting agent. As the main component, there are obtained 4.0 g of rac-1, 2, 3, 4, 4a$\alpha$, 5, 6, 10b$\beta$-octahydro-7-hydroxy-2$\alpha$-methylbenzo[f]quinoline-4-(3-propionylmethylcarboxylate) which is converted with 5N hydrogen chloride in ethanol into the hydrochloride, m.p. 207°–210°, yield 3.6 g (81%).

EXAMPLE 31

2.8 g (13 mmol) of rac-1, 2, 3, 4, 4a$\alpha$, 5, 6, 10b$\beta$-octahydro-2$\alpha$-methylbenzo[f]quinolin-7-ol in 100 ml of ethyl methyl ketone are heated to reflux for 20 hours with 5.5 g (26 mmol) of 4-chloro-4'-methoxybutyrophenone, 3.6 g of potassium carbonate and 0.9 g of sodium iodide. Subsequently, the mixture is cooled and partitioned between methylene chloride and water. After drying over magnesium sulfate and evaporation of the solvent under reduced pressure, there is obtained a crude product which is chromatographed on silica gel with ethyl acetate as the eluting agent and yields 1.9 g of the base as the main fraction. From ethyl acetate/hydrogen chloride/ethanol there crystallize 2.0 g (38%) of rac-[1, 2, 3, 4, 4a, 5, 6, 10b$\beta$-octahydro-2$\alpha$-methyl-7-hydroxybenzo[f]quinolin-4-yl]-4'-methoxybutyrophenone hydrochloride, m.p. 95°–97°.

EXAMPLE 32

4.05 g (15 mmol) of rac-1, 2, 3, 4, 4a$\alpha$, 5, 6, 10b$\beta$-octahydro-2$\alpha$-methylbenzo[f]quinolin-7-ol in 150 ml of acetone are heated to reflux for 4 hours with 3.6 ml (25 mmol) of ethyl 4-bromobutyrate, 5.75 g of potassium carbonate and 2.8 g of sodium iodide. Subsequently, the mixture is cooled and partitioned between methylene chloride and water. After drying over magnesium sulfate and evaporation of the solvent under reduced pressure, there is obtained a crude product which is chromatographed on silica gel with methylene chloride/methanol (98:2) and yields as the main fraction 3.65 g of the base. From methanol/hydrogen chloride/ethanol there crystallize 3.86 g (70%) of ethyl rac-1, 2, 3, 4, 4a, 5, 6, 10b$\beta$-octahydro-2$\alpha$-methyl-7-hydroxybenzo[f]quinoline-4-butyrate hydrochloride, m.p. 233°–235°.

EXAMPLE 33

A solution of 2.3 g (7.6 mmol) of rac-1, 2, 3, 4, 4a$\alpha$, 5, 6, 10b$\beta$-octahydro-7-hydroxy-2$\alpha$-methylbenzo[f]quinoline-4-(3-propionylmethylcarboxylate) in 30 ml of tetrahydrofuran is added dropwise to a suspension of 0.58 g of lithium aluminum hydride in 30 ml of dry tetrahydrofuran and the mixture is heated to reflux for 1 hour. After cooling to 5°, the mixture is hydrolyzed with saturated ammonium chloride solution, diluted with ethyl acetate and filtered. The filtrate is partitioned between saturated sodium bicarbonate solution and ethyl acetate. The organic phase is dried over magnesium sulfate and evaporated under reduced pressure. The residue is dissolved in 50 ml of methylene chloride/methanol and treated with 5N hydrogen chloride in ethanol. Concentration to a volume of 15 ml yields 11 g (46%) of rac-1, 2, 3, 4, 4a,$\alpha$, 5, 6, 10b$\beta$-octahydro-7-hydroxy-2$\alpha$-methylbenzo[f]quinoline-4-propanol hydrochloride, m.p. 248°–250°.

EXAMPLE 34

A solution of 1.4 g (3.6 mmol) of rac-[1, 2, 3, 4, 4a$\alpha$, 5, 6, 10b$\beta$-octahydro-7-hydroxy-2$\alpha$-methylbenzo[f]quinolin-4-yl]-4'-fluorobutyrophenone in 60 ml of tetrahydrofuran is added dropwise to a suspension of 0.7 g of sodium borohydride in 10 ml of methanol and the mixture is stirred at 20° for 1 hour. Thereafter, the mixture is hydrolyzed with 100 ml of water, extracted with methylene chloride and the organic phase is dried over magnesium sulfate and evaporated under reduced pressure. The residue is dissolved in 40 ml of ethyl acetate and treated with 5N hydrogen chloride in ethanol, whereby there is obtained 0.65 g (43%) of rac-1, 2, 3, 4, 4a$\alpha$, 5, 6, 10b$\beta$-octahydro-7-hydroxy-2$\alpha$-methylbenzo[f]quinoline-4-(4-fluorophenyl)-butanol hydrochloride, m.p. 123°–133°.

EXAMPLE 35

2.7 g (6.7 mmol) of rac-1, 2, 3, 4, 4a$\alpha$, 5, 6, 10b$\beta$-octahydro-2$\alpha$-(bromomethyl)-4-phenylethylbenzo[f]quinolin-7-ol are dissolved in 200 ml of methanol and 20 ml of glacial acetic acid and hydrogenated at 20° and under normal pressure for 39 hours in the presence of 0.3 g of palladium/carbon (10%). Subsequently, the catalyst is filtered off and the filtrate is evaporated under reduced pressure. The residue is partitioned between saturated sodium bicarbonate solution and methylene chloride. The organic phase is dried over magnesium sulfate and evaporated to dryness. The crystalline residue is dissolved in 100 ml of ethanol and treated with 6N hydrogen chloride in ethanol. From the solution there crystallize 1.8 g (75%) of white crystals of rac-1, 2, 3, 4, 4a$\alpha$, 5, 6, 10b8-octahydro-2$\alpha$-methyl-4-phenylethylbenzo[f]-quinolin-7-ol hydrochloride, m.p. 285°–287°.

The rac-1, 2, 3, 4, 4a$\alpha$, 5, 6, 10b$\beta$-octahydro-2$\alpha$-(bromomethyl)-4-phenylethylbenzo[f]quinolin-7-ol used as the starting material was prepared as follows:

8.2 g (65.4 mmol) of phenylethylamine are dissolved in 30 ml of benzene and there is added thereto at 0°–5° within 1 hour a solution of 9.9 g (43.6 mmol) of ethyl 2-(bromomethyl)acrylate (85%) in 40 ml of benzene, which was prepared according to the details of J. Villieras and M. Rambaud, Synthesis 1982, 924–926. After stirring at 0°–5° for 1 hour, a solution of 6.4 g (36.3 mmol) of 5-methoxy-2-tetralone in 30 ml of benzene is added dropwise and the mixture is subsequently heated to reflux on a water separator for 20 hours. After cooling, the mixture is partitioned between ethyl acetate and water and the organic phase is dried over magnesium sulfate. Distillation of the volatile constituents under reduced pressure gives 16.8 g of a dark oil which is chromatographed on silica gel with ether/n-hexane (1:4). As the main fraction, there are obtained 10.05 g of a yellow oil. The oil (25.7 mmol) is dissolved in 100 ml of tetrahydrofuran and 10 ml of alcohol and there are added thereto 3.2 g (51.4 mmol) of sodium cyanoborohydride and sufficient 6.3N hydrogen chloride in ethanol (a total of 5.3 ml) such that the reaction solution remains at the transition point of bromocresol green. After stirring at 20°–30° for 4 hours, the mixture is poured into a sodium bicarbonate solution and extracted with methylene chloride. After washing the organic phase with water, it is dried over magnesium sulfate and evaporated under reduced pressure. The oily residue is chromatographed on silica gel and eluted firstly with a 1:2 mixture of methylene chloride and n-hexane, then with methylene chloride. The fractions which are uniform according to thin-layer chromatography [elution system a) diethyl ether/n-hexane (1:1) or b) methylene chloride/diethyl ether (9:1)] are combined and evaporated, whereby 3.7 g (37%) of ethyl rac-1, 2, 3, 4, 4a$\alpha$, 5, 6, 10b$\beta$-octahydro-4-phenylethyl-7-methoxy-benzo[f]quinoline-2$\alpha$-carboxylate are obtained as an orange-red oil.

3.7 g (9.4 mmol) of ethyl rac-1, 2, 3, 4, 4a$\alpha$, 5, 6, 10b$\beta$-octahydro-4-phenylethyl-7-methoxy-benzo[f]quinoline-2$\alpha$-carboxylate in 50 ml of dry tetrahydrofuran are added dropwise to a suspension of 1.2 g of lithium aluminum hydride in 50 ml of dry tetrahydrofuran and subsequently stirred at 20°–32° for 3/4 hour. After hydrolysis of the reaction solution with 50 ml of ammonium chloride solution at 0°–10°, the mixture is filtered over siliceous earth and extracted with ethyl acetate and methylene chloride. Drying of the combined organic extracts over magnesium sulfate and distillation of the solvent under reduced pressure yield 3.25 g (98%) of rac-1, 2, 3, 4, 4aα, 5, 6, 10bβ-octahydro-2α-(hydroxymethyl)-4-phenylethyl-7-methoxybenzo[f]quinoline.

3.25 g (9.2 mmol) of rac-1, 2, 3, 4, 4aα, 5, 6, 10bβ-octahydro-2α-(hydroxymethyl)-4-phenylethyl-7-methoxybenzo[f]quinoline are heated to reflux for 4 hours in 300 ml of hydrobromic acid (48%). Subsequently, the volatile constituents are evaporated under reduced pressure. Then, 70 ml of toluene are added twice thereto and the mixture is evaporated each time. The residue is partitioned between saturated sodium bicarbonate solution and methylene chloride and the combined extracts are dried over magnesium sulfate and evaporated. The residue (4.6 g) is chromatographed on silica gel and there are obtained from the fractions eluted with ethyl acetate 3.15 g (85%) of pale brown crystals of rac-1, 2, 3, 4, 4aα, 5, 6, 10bβ-octahydro-2α-(bromomethyl)-4-phenylethylbenzo[f]quinolin-7-ol. Recrystallization from ethyl acetate yields beige crystals of melting point 160°-162°.

EXAMPLE 36

5.2 g (20 mmol) of rac-1, 2, 3, 4, 4aα, 5, 6, 10bβ-octahydro-2α-methyl-4-propylbenzo[f]quinolin-7-ol are dissolved in 100 ml of methanol and 100 ml of methylene chloride and treated with 3.85 g (11.1 mmol) of (+)-2, 2'-(1, 1'-binaphthyl)phosphoric acid in 100 ml of methanol and 100 ml of methylene chloride and evaporated under reduced pressure to a volume of 100 ml. From the solution there then crystallize 6.3 g of beige crystals which are recrystallized three times from ethanol/methanol/chloroform (1:1:1). The residual 2.3 g of crystals (m.p.>300°) are partitioned between diethyl ether and dilute ammonia solution. The organic phase is dried over magnesium sulfate and evaporated. Then, 0.8 g of the optically active base (m.p. 178°-187°) is converted with hydrogen chloride in ethanol into the hydrochloride. There is thus obtained 0.7 g (25%) of white crystals of (+)-1, 2, 3, 4, 4aα, 5, 6, 10bβ-octahydro-2α-methyl-4propylbenzo[f]quinolin-7-ol hydrochloride, m.p. 275°-277°, $[\alpha]_D = +67.4°$ (c=1% in methanol).

All mother liquors from the crystallization described above are partitioned between diethyl ether and dilute ammonia solution. The organic phase is dried over magnesium sulfate and evaporated. The residue (3.75 g of base) is dissolved in 200 ml of methylene chloride/methanol (1:1) and treated with 4.52 g (13 mmol) of (-)-2, 2'-(1, 1'-binaphthyl)phosphoric acid in 200 ml of methylene chloride/methanol (1:1). After concentration under reduced pressure to a volume of 140 ml, there crystallize out 6.9 g of beige crystals which are recrystallized three times from ethanol/methanol/chloroform (1:1:1). There are finally obtained 3.6 g of crystals (m.p.>300°) which are partitioned between diethyl ether and dilute ammonia solution. From the organic phase, there are obtained after drying over magnesium sulfate, filtration and concentration, 1.5 g of the optically active base (m.p. 176°-187°) which are converted with hydrogen chloride in ethanol into the hydrochloride, whereby there are obtained 1.45 g (52%) of white crystals of (-)-1, 2, 3, 4, 4aα, 5, 6, 10bβ-octahydro-2α-methyl-4-propylbenzo[f]quinolin-7-ol hydrochloride, m.p. 275°-277°, $[\alpha]_D = -68.4°$ (c=1% in methanol).

EXAMPLE 37

A suspension of 2.7 g (9.1 mmol) of rac-1, 2, 3, 4, 4aα, 5, 6, 10bβ-octahydro-2α-methyl-4-propylbenzo[f]quinolin-7-ol hydrochloride in 50 ml of methylene chloride and 8.4 ml (60 mmol) of triethylamine is treated at 20° with 1.76 ml (22 mmol) of pivaloyl chloride in 10 ml of methylene chloride and stirred for 15 hours. Subsequently, the reaction solution is partitioned between saturated sodium bicarbonate solution and methylene chloride and the pH value of the aqueous phase is adjusted to 8 with 2N sodium hydroxide solution. After drying the organic phase over magnesium sulfate, it is evaporated. The residue is chromatographed on silica gel with methylene chloride/methanol (98:2). There are eluted 3.6 g of oily product which crystallizes as the hydrochloride from methanol/ethyl acetate after the addition of hydrogen chloride in ethanol. In this manner there are obtained 3.15 g (91%) of rac 1, 2, 3, 4, 4aα, 5, 6, 10bβ-octahydro-2α-methyl-4-propylbenzo[f]quinolin-7-yl pivalate hydrochloride, m.p. 222°-224°.

EXAMPLE 38

3.05 g (16 mmol) of (-)-1, 2, 3, 4, 4aα, 5, 6, 10bβ-octahydro-2α-methyl-7-methoxybenzo[f]quinoline in 35 ml of methylene chloride and 4.7 ml of triethylamine are treated at 20° while stirring with 2 g (19 mmol) of methoxyacetyl chloride in 15 ml of methylene chloride. After 18 hours at 20°, the mixture is partitioned between methylene chloride and sodium bicarbonate solution and the organic phase is dried over magnesium sulfate and evaporated under reduced pressure. The residual oil (5.2 g) is chromatographed on silica gel.

Elution with ethyl acetate/n-hexane (1:2) yields the main fraction (3.1 g) which is dissolved in 55 ml of dry tetrahydrofuran and reduced with 0.8 g of lithium aluminum hydride (heating to reflux for 1 hour). For the working-up, the mixture is hydrolyzed with 10 ml of saturated ammonium chloride solution, diluted with 50 ml of ethyl acetate and filtered through siliceous earth. After drying the organic phase over magnesium sulfate, it is evaporated. The residue is chromatographed on silica gel with methylene chloride/methanol (99:1). There are eluted as the main fraction 2.3 g of oil which are dissolved in 90 ml of hydrobromic acid (48%) and heated to reflux for 1 hour. Subsequently, the volatile constituents are distilled off under reduced pressure and the residue is partitioned between methylene chloride and dilute sodium hydroxide solution at pH 8. The organic phase is dried over magnesium sulfate and evaporated. The residue is treated in methanol with hydrogen chloride and crystallized by the addition of ethyl acetate. There are thus obtained 1.5 g (32%) of beige crystals of (-)-1, 2, 3, 4, 4aα, 5, 6, 10bβ-octahydro-2α-methyl-7-hydroxybenzo[f]-quinoline-4-ethanol hydrochloride, m.p. 239°-241°, $[\alpha] = -67.1°$ (c=1% in methanol).

EXAMPLE 39

10 g (43 mmol) of rac-1, 2, 3, 4, 4aα, 5, 6, 10bβ-octahydro-2α-methyl-7-methoxybenzo[f]quinoline in 300 ml of ethyl methyl ketone are heated to reflux for 20 hours with 8 ml of 2-chlorocyclopentanone, 11 g of potassium carbonate and 2 g of sodium iodide. Subsequently, the volatile constituents are distilled off under reduced pressure and the residue is partitioned between water and methylene chloride. The residue from the organic phase is chromatographed on silica gel with methylene chloride/methanol (99:1) as the eluting agent, whereby there are obtained 12.4 g (92%) of rac-1, 2, 3, 4, 4aα, 5, 6, 10bβ-octahydro-2α-methyl-4-(2-cyclopentanonyl)-7-methoxybenzo[f]quinoline, m.p. 126°–128°.

3 g (9.4 mmol) of rac-1, 2, 3, 4, 4aα, 5, 6, 10bβ-octahydro-2α-methyl-4-(2-cyclopentanonyl)-7-methoxybenzo[f]quinoline are heated to reflux (internal temperature 214°) for 2 hours with 1. ml of hydrazine hydrate, 2.24 g of powdered potassium hydroxide and 10 ml of triethylene glycol. Thereafter, the flask is fitted with a rising condenser. A mixture of hydrazine and water is distilled off slowly and the reaction mixture is held at an internal flask temperature of 195° for a further 2 hours. After cooling, the mixture is poured into water and extracted with methylene chloride. The residue from the organic phase is chromatographed on silica gel with methylene chloride/methanol (19:1) as the eluting agent and the 1.6 g of base (56%) obtained is converted with hydrogen chloride in ethanol into the hydrochloride, whereby there crystallize out 1.5 g of rac-1, 2, 3, 4, 4aα, 5, 6, 10bβ-octahydro-4-cyclopentyl-2α-methyl[f]quinolin-7-ol hydrochloride, m.p.>310°.

EXAMPLE 40

8.0 g (34.5 mmol) of (-)-1, 2, 3, 4, 4aα, 5, 6, 10bβ-octahydro-2α-methyl-7-methoxybenzo[f]quinoline are heated to reflux in 250 ml of hydrobromic acid (48%) while stirring in an argon atmosphere for 1 hour. After cooling, the excess hydrobromic acid is distilled off under reduced pressure and the residue is partitioned between methylene chloride/methanol (5:1) and saturated aqueous sodium bicarbonate solution. The aqueous phase is adjusted to pH 9 with concentrated sodium hydroxide solution and the organic phase is separated. After three-fold extraction of the aqueous phase with methylene chloride, the organic extracts are combined, dried over anhydrous magnesium sulfate and evaporated under reduced pressure. The crystalline residue (7.0 g; 93%) is dissolved in 150 ml of methanol, filtered and acidified with hydrogen chloride in ethanol. Upon concentration of the solution to a volume of 75 ml, there crystallizes out (-)-1, 2, 3, 4, 4aα, 5, 6, 10bβ-octahydro-2α-methylbenzo[f]quinolin-7-ol hydrochloride, m.p. 300°–305°, = −86.0° (c=1% in methanol).

EXAMPLE A 10 mg Tablets

Composition

| Composition | |
|---|---|
| 1. (−)-1,2,3,4,4aα,5,6,10bβ-Octahydro-2α-methyl-7-hydroxybenzo[f]quinoline-4-ethanol hydrochloride | 11.38 mg* |
| 2. Powdered lactose | 98.62 mg |
| 3. Maize starch | 45.00 mg |
| 4. Polyvinylpyrrolidone K 30 | 15.00 mg |
| 5. Maize starch | 25.00 mg |
| 6. Talc | 4.50 mg |
| 7. Magnesium stearate | 0.50 mg |
| Tablet weight | 200.00 mg |

*corresponding to 10 mg of base

Procedure

1–3 are mixed and sieved through a sieve having a mesh size of 0.5 mm. This powder mixture is moistened with an alcoholic solution of 4 and kneaded. The moist mass is granulated, dried and converted into a suitable particle size. To the dried granulate are added in succession 5, 6 and 7 and mixed. The ready-to-press mixture is pressed to tablets of suitable size having a required weight of 200 mg.

EXAMPLE B 20 mg Interlocking Gelatin Capsules

Composition

| Composition | |
|---|---|
| 1. (−)-1,2,3,4,4aα,5,6,10bβ-Octahydro-2α-methyl-7-hydroxybenzo[f]quinoline-4-ethanol hydrochloride | 22.76 mg* |
| 2. Powdered lactose | 63.24 mg |
| 3. Maize starch | 40.00 mg |
| 4. Talc | 3.60 mg |
| 5. Magnesium stearate | 0.40 mg |
| 6. Cryst. lactose | 110.00 mg |
| Capsule fill weight | 240.00 mg |

*corresponding to 20 mg of base

Procedure

1–5 are mixed and sieved through a sieve having a mesh size of 0.5 mm. Thereafter, 6 is added and mixed. This ready-to-fill mixture is filled into interlocking gelatin capsules of suitable size (e.g. No. 2) having an individual fill weight of 240 mg.

EXAMPLE C

When the procedures described in Examples A and B are followed, corresponding tablets and, respectively, capsules can be prepared from the following, also preferred, compounds:

rac-1, 2, 3, 4, 4aα, 5, 6, 10bβ-Octahydro-2α-methyl-4-propylbenzo[f]quinolin-7-ol, (-)-1, 2, 3, 4, 4aα, 5, 6, 10bβ-octahydro-2α-methyl-4-propylbenzo[f]quinolin-7-ol, rac-1, 2, 3, 4, 4aα, 5, 6, 10bβ-octahydro-4-isopropyl-2α-methylbenzo[f]quinolin-7-ol, rac-1, 2, 3, 4, 4aα, 5, 6, 10bβ-octahydro-4-cyclopentyl-2α-methylbenzo[f]quinolin-7-ol, (-)-1, 2, 3, 4, 4aα, 5, 6, 10bβ-octahydro-4-cyclopentyl-2α-methylbenzo[f]quinolin-7-ol, rac-1, 2, 3, 4, 4aα, 5, 6, 10bβ-octahydro-7-hydroxy-2α-methylbenzo[f]quinoline-4-ethanol, or (-)-1, 2, 3, 4, 4aα, 5, 6, 10bβ-octahydro-2α-methylbenzo[f]quinolin-7-ol.

We claim:

1. A compound of the formula

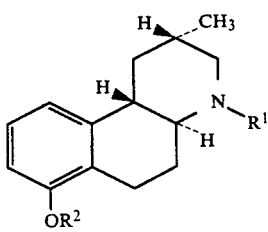

I wherein $R^1$ is hydrogen; lower-alkyl, unsubstituted or substituted by hydroxy, lower-alkoxy, cyano, halogen, lower-alkoxycarbonyl, aminocarbonyl, substituted benzoyl or substituted α-hydroxybenzyl; lower-alkenyl;

cycloalkyl; cycloalkyl-lower-alkyl; heteroaryl-loweralkyl; or aryl-lower-alkyl, unsubstituted or substituted by hydroxy, lower-alkoxy, lower-alkyl or halogen, and R² is hydrogen or lower-alkanoyl, an enantiomer or the racemate thereof, or a pharmaceutically acceptable acid addition salt of such a compound.

2. A compound in accordance with claim 1, wherein R² is hydrogen or acetyl.

3. A compound in accordance with claim 2, wherein R² is hydrogen.

4. A compound in accordance with claim 3, wherein R¹ is hydrogen; lower-alkyl, unsubstituted or substituted by hydroxy, cyano or substituted benzoyl; cycloalkyl; cycloalkylalkyl; or aryl-lower-alkyl, unsubstituted or substituted by hydroxy.

5. A compound in accordance with claim 4, wherein R¹ is hydrogen; lower-alkyl, unsubstituted or substituted by hydroxy, cyano or 4-methoxybenzoyl; cyclopentyl; cyclopentylethyl or 4-hydroxyphenethyl.

6. A compound in accordance with claim 5, wherein the lower-alkyl group is ethyl, propyl or isopropyl.

7. A compound in accordance with claim 6, wherein R¹ is hydrogen; ethyl propyl or isopropyl, which can be optionally substituted by hydroxy, cyano or 4-methoxybenzoyl: cyclopentyl; cyclopentylethyl or 4-hydroxyphenethyl and R² is hydrogen.

8. A compound, in accordance with claim 1, which is selected from the group consisting of rac-1, 2, 3, 4, 4aα, 5, 6, 10bβ-Octahydro-2α-methyl-4-propylbenzo[f]quinolin-7-ol, rac-1, 2, 3, 4, 4aα, 5, 6, 10bβ-octahydro-4-(4-hydroxyphenethyl)-2α-methylbenzo[f]-quinolin-7-ol, rac-1, 2, 3, 4, 4aα, 5, 6, 10bβ-octahydro-7-hydroxy-2α-methylbenzo[f]quinoline-4-ethanol, rac-1, 2, 3, 4, 4aα, 5, 6, 10bβ-octahydro-7-hydroxy-2α-methylbenzo[f]-quinoline-4-butyronitrile, rac-1, 2, 3, 4, 4aα, 5, 6, 10bβ-octahydro-4-cyclopentyl-2α-methylbenzo[f]quinolin-7-ol, rac-1, 2, 3 4, 4α, 10bβ-octahydro-4-isopropyl-2α-methylbenzo[f]quinolin-7-ol, rac-1, 2, 3, 4, 4aα, 5, 6, 10bβ-octahydro-4-cyclopentylethyl-2α-methylbenzo[f]quinolin-7-ol, rac-[1, 2, 3, 4, 4aα, 5, 6, 10bβ-octahydro-7-hydroxy-2α-methylbenzo[f]quinolin-4-yl]-4'-methoxybutyrophenone and rac-1, 2, 3 4, 4aα, 5, 6, 10bβ-octahydro-2α-methylbenzo[f]quinolin-7-ol.

9. The compound in accordance with claim 1, (-)-1, 2, 3, 4, 4aα, 5, 6, 10bβ-Octahydro-4-cyclopentyl-2α-methylbenzo[f]quinolin-7-ol.

10. The compound, in accordance with claim 1, (-)- 1, 2, 3, 4, 4aα, 5, 6, 10bβ-Octahydro-2α-methyl-4-propylbenzo[f]quinolin-7-ol.

11. The compound in accordance with claim 1, (-) 1, 2, 3, 4, 4aα, 5, 6, 10bβ-Octahydro-7-hydroxy-2α-methylbenzo[f]quinoline-4-ethanol.

12. The compound, in accordance with claim 1, (-)-1, 2, 3, 4, 4aα, 5, 6, 10bβ-Octahydro-2α-methylbenzo[f]quinolin-7-ol.

13. A compound selected from the group consisting of compounds of the formulas

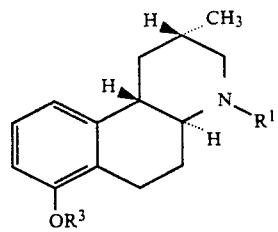

II

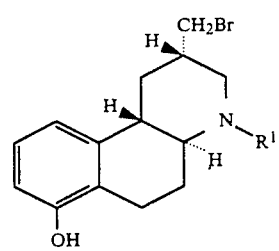

III

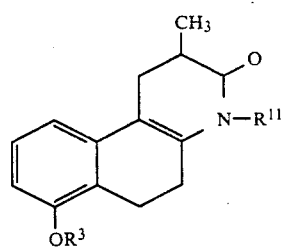

V

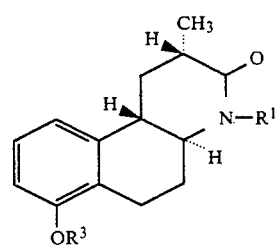

VI

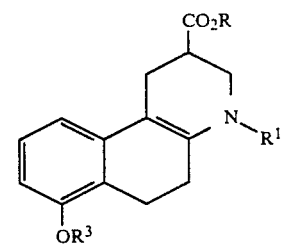

IX

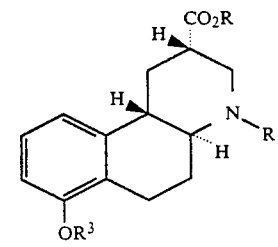

X and

-continued

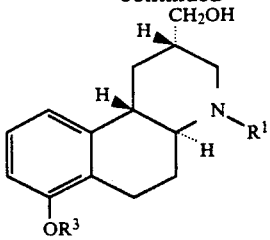

wherein R is lower-alkyl, R¹ is hydrogen; lower-alkyl, unsubstituted or substituted by hydroxy, lower-alkoxy, cyano, haloqen, lower-alkoxycarbonyl aminocarbonyl, substituted benzoyl or substituted α-hydroxybenzyl; lower-alkenyl; cycloalkyl; cycloalkyl-lower-alkyl; heteroaryl-lower-alkyl; or aryl-lower-alkyl, unsubstituted or substituted by hydroxy, lower-alkoxy, lower-alkyl or halogen, R³ is lower-alkyl and is hydrogen or benzyl.

14. A pharmaceutical composition which comprises an effective amount of a compound of the formula

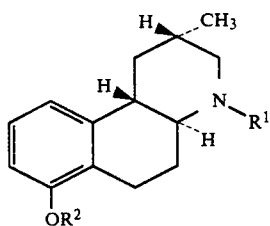

wherein R¹ is hydrogen; lower-alkyl, unsubstituted or substituted by hydroxy, lower-alkoxy, cyano, halogen, lower-alkoxycarbonyl. aminocarbonyl, substituted benzoyl or substituted α-hydroxybenzyl; lower-alkenyl; cycloalkyl; cycloalkyl-lower-alkyl; heteroaryl-lower-alkyl; or aryl-lower-alkyl, unsubstituted or substituted by hydroxy, lower-alkoxy, lower-alkyl or halogen, and R is hydrogen or lower-alkanoyl, an enantiomer or the racemate thereof, or a pharmaceutically acceptable acid addition salt of such a compound and an inert carrier.

15. A pharmaceutical composition in accordance with claim 14, wherein R² is hydrogen or acetyl.

16. A pharmaceutical composition in accordance with claim 15, wherein R² is hydrogen 17. A pharmaceutical composition in accordance with claim 16, wherein R¹ is hydrogen; lower-alkyl, unsubstituted or substituted by hydroxy, cyano or substituted benzoyl; cycloalkyl; cycloalkylalkyl; or aryl-lower-alkyl, unsubstituted or substituted by hydroxy.

18. A pharmaceutical composition in accordance with claim 17, wherein R¹ is hydrogen; lower-alkyl, unsubstituted or substituted by hydroxy, cyano or 4-methoxybenzoyl; cyclopentyl; cyclopentylethyl or 4-hydroxyphenethyl.

19. A pharmaceutical composition in accordance with claim 18, wherein the lower-alkyl group is ethyl, propyl or isopropyl.

20. A pharmaceutical composition in accordance with claim 19, wherein R¹ is hydrogen; ethyl, propyl or isopropyl, which are optionally substituted by hydroxy, cyano or 4-methoxybenzoyl; cyclopentyl; cyclopentylethyl or 4-hydroxyphenethyl and R² is hydrogen 21. A pharmaceutical composition, in accordance with claim 14, wherein the compound of formula I is (-)-1, 2, 3, 4, 4aα, 5, 6, 10bβ-Octahydro-4-cyclopentyl-2α-methylbenzo[f]quinolin-7-ol.

22. A pharmaceutical composition, in accordance with claim 14, wherein the compound of formula I is (-)-1, 2, 3, 4, 4aα, 5, 6, 10bβ-Octahydro-2α-methy;4-propylbenzo[f]quinolin-7-ol.

23. A pharmaceutical composition, in accordance with claim 14, wherein the compound of formula I is (-)-1, 2, 3, 4, 4aα, 5, 6, 10bβ-Octahydro-7-hydroxy-2α-methylbenzo[f]quinoline-4-ethanol.

24. A pharmaceutical composition, in accordance with claim 14, wherein the compound of formula I is (-)-1, 2, 3, 4, 4aα, 5, 6, 10bβ-Octahydro-2α-methyl-benzo[f]quinolin-7-ol.

25. A method of treating psychotic disorders which comprises administering to a host requiring such treatment an effective amount of a compound of the formula

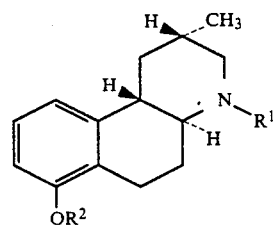

wherein R¹ is hydrogen; lower-alkyl, unsubstituted or substituted by hydroxy, lower-alkoxy, cyano, halogen, lower-alkoxycarbonyl, aminocarbonyl, substituted benzoyl or substituted α-hydroxybenzyl; lower-alkenyl; cycloalkyl; cycloalkyl-lower-alkyl; heteroaryl-lower-alkyl; or aryl-lower-alkyl, unsubstituted or substituted by hydroxy, lower-alkoxy, lower-alkyl or halogen, and R² is hydrogen or lower-alkanoyl, an enantiomer or the racemate thereof, or a pharmaceutically acceptable acid addition salt of such a compound.

26. A method in accordance with claim 25, wherein R² is hydrogen or acetyl.

27. A method in accordance with claim 26, wherein R² is hydrogen.

28. A method in accordance with claim 27, wherein R¹ is hydrogen; lower-alkyl, unsubstituted or substituted by hydroxy, cyano or substituted benzoyl; cycloalkyl; cycloalkylalkyl; or aryl-lower-alkyl, unsubstituted or substituted by hydroxy.

29. A method in accordance with claim 4, wherein R¹ is hydrogen; lower-alkyl, unsubstituted or substituted by hydroxy, cyano or 4-methoxybenzoyl; cyclopentyl; cyclopentylethyl or 4-hydroxyphenethyl.

30. A method in accordance with claim 5, wherein the lower-alkyl group is ethyl, propyl or isopropyl.

31. A method in accordance with claim 6, wherein R¹ is hydrogen; ethyl, propyl or isopropyl, which are optionally substituted by hydroxy, cyano or 4-methoxybenzoyl; cyclopentyl: cyclopentylethyl or 4-hydroxyphenethyl and R² is hydrogen.

32. A method in accordance with claim 25, wherein the compound of formula I is (-)-1, 2, 3, 4, 4aα, 5, 6, 10bβ-Octahydro-4-cyclopentyl-2α-methylbenzo[f]quinolin-7-ol.

33. A method in accordance with claim 25, wherein the compound of formula I is (-)-1, 2, 3, 4, 4aα, 5, 6, 10bβ-Octahydro-2α-methyl-4-propylbenzo[f]quinolin-7-ol.

34. A method in accordance with claim 25, wherein the compound of formula I is (-)-1, 2, 3, 4, 4aα, 5, 6, 10bβ-Octahydro-7-hydroxy-2α-methylbenzo[f]quinoline-4-ethanol.

35. A method in accordance with claim 25, wherein the compound of formula I is (-)-1, 2, 3, 4, 4aα, 5, 6, 10bβ-Octahydro-2α-methylbenzo[f]quinolin-7-ol.

* * * * *

UNITED STATES PATENT AND TRADEMARK OFFICE
CERTIFICATE OF CORRECTION

PATENT NO. : 5,030,636
DATED : July 9, 1991
INVENTOR(S) : Rene Imhof and Hans Hermann Keller It is certified that error appears in the above-identified patent and that said Letters Patent is hereby corrected as shown below:

In claim 13, column 33, line 19, please delete "and is hydrogen" and insert therefor --- and $R^{11}$ is hydrogen ---.

In claim 14, column 33, line 38, please delete "R is hydrogen" and insert therefor --- $R^2$ is hydrogen --- .

Signed and Sealed this

Fourth Day of May, 1993

Attest:

MICHAEL K. KIRK

Attesting Officer

Acting Commissioner of Patents and Trademarks